(12) United States Patent
Hartwig et al.

(10) Patent No.: US 6,384,282 B2
(45) Date of Patent: May 7, 2002

(54) TRANSITION METAL-CATALYZED PROCESS FOR ADDITION OF AMINES TO CARBON-CARBON DOUBLE BONDS

(75) Inventors: John F. Hartwig, Durham, CT (US); Motoi Kawatsura, Chatham, NJ (US); Oliver Loeber, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/793,212

(22) Filed: Feb. 26, 2001

Related U.S. Application Data

(60) Provisional application No. 60/186,004, filed on Mar. 1, 2000.

(51) Int. Cl.$^7$ .......................... C07C 209/60; G01J 3/46; G01N 21/25

(52) U.S. Cl. ................. 564/485; 564/305; 564/408; 356/402; 356/408

(58) Field of Search .................. 564/305, 408, 564/485; 356/402, 408

(56) References Cited

U.S. PATENT DOCUMENTS

| | | | |
|---|---|---|---|
| 4,120,901 A | 10/1978 | Hobbs | 260/585 D |
| 4,307,250 A | 12/1981 | Peterson | 564/445 |
| 5,929,265 A | 7/1999 | Dorta et al. | 556/14 |
| 5,977,361 A | 11/1999 | Hartwig et al. | 544/264 |
| 6,048,993 A | 4/2000 | Grubbs et al. | 556/21 |
| 6,057,456 A | 5/2000 | Hartwig et al. | 548/540 |
| 6,072,073 A | 6/2000 | Kawatsura et al. | 560/82 |
| 6,100,000 A | 8/2000 | Hartwig et al. | 544/264 |

OTHER PUBLICATIONS

Muller et al., "Metal–Initiated Amination of Alkenes and A;kynes", *Chem. Rev.* 1988, 98, pp. 675–703.
Gasc et al., "Amination of Alkenes", *Tetrahedron Report No. 144*, vol. 19, No. 5, pp. 703–731, (1982).
Li–Biao Han et al., "Transition metal–catalyzed addition reactions of H–heteroatom and inter–heteroatom bonds to carbon–carbon unsaturated linkages via oxidative additions", *Chem. Commun*, 1999, pp. 395–402.
Tian et al., "Constrained Geometry Organolanthanide Catalysts. Synthesis, Structural Characterization, and Enhanced Aminoalkene Hydroamination/Cyclization Activity", *OrganometallicsI 1999*, 18, pp. 2568–2570.
Arredondo et al., "Organolanthanide–Catalyzed Hydroamination/Cyclization. Efficient Allene–Based Transformations for the Synthesis of Naturally Occurring Alkaloids", *J. Am. Chem. Soc.*, 1999, 121, pp. 3633–3639.
Li et al., "Organolanthanide–Catalyzed Intramolecular Hydroamination/Cyclization of Aminoalkynes", *J. Am. Chem. Soc.*, 1996, 118, pp. 9295–9306.
Coulson, "Catalytic Addition of Secondary Amines to Ethylene", *Tetrahedron Letters*, No. 5, 1971, pp. 429–430.

Beller et al., "Anti–Markovinov Functionalizations of Unsaturated Compounds, Part 5, The First Rhodium–Catalyzed Ati–Markovnikov Hydroamination: Studies on Hydroamination and Oxidative Amination of Aromatic Olefins", *Chem. Eur. J.* 1999, No. 4, pp. 1306–1319.
Beller et al., Anti–Markonikov Reactions, 6, Rhodium–Catalyzed Amination of Vinylpyridines: Hydroamination versus Oxidative Amination, *Eur. J. Inorg. Chem.* 1999, pp. 1121–1132.
Dorta et al., "The {IrCl(Diphosphine)]$_2$/Fluoride System. Developing Catalytic Asymmetric Olefin Hydroamination", *J. Am. Chem. Soc.*, 1997, 119, pp. 10857–10858.
Seligson et al., "Protonolysis Approach to the Catalytic Amination of Olefins with (Bis(phosphine)palladium(II) Dialkyls", *Organometallics* 1993, 12, pp. 744–751.
Casalnuovo, "Rational Design in Homogeneous Catalysis. Ir(I)–Catalyzed Addition of Aniline to Norbornylene via N–H Activation", *J. Am. Chem. Soc.* 1988, 110, pp. 6738–6744.
Kawatsura et al., "Palladium–Catalyzed Hydroamination of Vinylarenes Using Arylamines", *J. Am. Chem. Soc.*, 2000, 122, pp. 9546–9547.
Sibi et al., "Chiral Lewis Acid Catalysis in Conjugate Additions of O–Benzylhydroxylamine to Unsaturated Amides. Enantioselective Synthesis of β–Amino Acid Precursors", *J. Am. Chem. Soc.*, 1998, 120, 6615–6616.
Guerin et al., "Amine–Catalyzed Addition of Azide Ion to a β–Unsaturated Carbonyl Compounds", *Organic Letters*, 1999, vol. 1, No. 7, pp. 1107–1109.
Myers et al., "Asymmetric Synthesis of β–Amino Acid Derivatives via Catalytic Conjugate Addition of Hydrazoic Acid to Unsaturated Imides", *J. Am. Chemical Soc.*, 1999, 121, pp. 8959–8960.
Andell et al., "Nickel– and Palladium–Catalyzed Additions of Nucleophiles to Cyclic 1,3–Dienes", *Acta Chemica Scandinavica*, 40, 1986, pp. 184–189.
Baker et al., "Reaction of Amines with 1,3–Dienes catalysed by Nickel Complexes", *J.C. Perkins II*, 1974, pp. 1511–1517.

(List continued on next page.)

*Primary Examiner*—Brian J. Davis
(74) *Attorney, Agent, or Firm*—Todd E. Garabedian; Wiggin & Dana

(57) ABSTRACT

The present invention is directed to a process for addition of amines to carbon-carbon double bonds in a substrate, comprising: reacting an amine with a compound containing at least one carbon-carbon double bond in the presence a transition metal catalyst under reaction conditions effective to form a product having a covalent bond between the amine and a carbon atom of the former carbon-carbon double bond. The transition metal catalyst comprises a Group 8 metal and a ligand containing one or more 2-electron donor atoms. The present invention is also directed to enantioselective reactions of amine compounds with compounds containing carbon-carbon double bonds, and a calorimetric assay to evaluate potential catalysts in these reactions.

44 Claims, 2 Drawing Sheets

OTHER PUBLICATIONS

Al-Massum et al., "The Two Component Palladium Catalyst System for Intermolecular Hydroamination of Allenes", *Tetrahedron Letter*, vol. 38, No. 34, pp. 6071–6074, 1997.

Besson et al., "Synthesis of Allylic Amines Through the Palladium-Catalyzed Hydroamination of Allenes", *Tetrahedron Letters*, vol. 36, No. 22, 1995, pp. 3857–3860.

Kiji et al., "Nickel–Catalyzed Amination of 1,3–Dienes Evidence For A π–Allyl Intermediate", *Journal of Organometallic Chemistry*, 77, 1974, pp. 125–130.

Jolly, "$\eta^3$–Allypalladium Compounds", *Angew, Chem. Int. Ed. Engl.*, 24, 1985, pp. 283–295.

Petrushkina, E.A.; Zakharkin, L.I., "The reaction of isoprene with aniline on complex palladium catalysts", *Izv. Akad. Nauk, Ser. Khim.* 1992, p. 1794.

Dzhemilev et al., *Akad. Nauk. SSSR. Khim*, 1976, p. 2346.

Dzhemilev et al., *Akad. Nauk. SSSR. Khim*, 1978, p. 1068.

Dzhemilev et al., *Akad. Nauk. SSSR. Khim*, 1978, p. 1412.

Dzhemilev et al., *Zh. Org. Khim.* 1979, 15, p. 1164.

TRANSITION METAL-CATALYZED PROCESS FOR ADDITION OF AMINES TO CARBON-CARBON DOUBLE BONDS

CROSS-REFERENCE TO RELATED APPLICATIONS

This application claims the benefit of U.S. Provisional Application No. 60/186,004 filed Mar. 1, 2000.

STATEMENT OF GOVERNMENT SUPPORT

This application was made with United States Government support under Award Number R29-GM55382 from the National Institutes of Health and Award Number DE-FG02-96ER14678 from the Department of Energy. The U.S. Government has certain rights in this invention.

BACKGROUND OF THE INVENTION

1. Field of the Invention

This invention relates to a process for addition of amines to carbon-carbon double bonds, and more particularly to a process of adding amines to carbon-carbon double bonds in an enantioselective manner. The method of the invention utilizes a transition metal catalyst made from a Group 8 metal and a ligand containing one or more 2-electron donor atoms. The present invention is also directed to a colorimetric assay to evaluate potential catalysts in these reactions.

2. Brief Description of the Related Art

The metal-catalyzed addition of amines to carbon-carbon double bonds is an unsolved, synthetically important problem (Muller, T. E.; Beller, M. *Chem. Rev.* 1998, 98, 675–703; Han, L.-B.; Tanaka, M. *Chem Commun* 1999, 395–402; Gasc, M. B.; Lattes, A.; Perie, J. J. *Tetrahedron* 1983, 39, 703–731). Recent advances have been made using lanthanide (Tian, S.; Arredondo, V. M.; Stern, C. L.; Marks, T. J. *Organometallics* 1999, 18, 2568–2570; Arredondo, V. M.; Tian, S.; McDonald, F. E.; Marks, T. J. *J. Am. Chem Soc.* 1999, 121, 3633–3639; Li, Y. W.; Marks, T. J. *J. Am. Chem. Soc.* 1996, 118, 9295–9306) and precious metal complexes, (Coulson, D. R. *Tetrahedron Lett.* 1971, 429–430; Beller, M.; Trauthwein, H.; Eichberger, M.; Breindl, C.; Herwig, J.; Muller, T. E.; Thiel, O. R. *Chem. Eur. J.* 1999, 5, 1306–1319; Beller, M.; Trauthwein, H.; Eichberger, M.; Breindl, C.; Müller, T., E. *Eur. J. Inorg. Chem.* 1999, 1121–1132; Casalnuovo, A. L.; Calabrese, J. C.; Milstein, D. *J. Am. Chem. Soc.* 1988, 110, 6738–6744; Dorta, R.; Egli, P.; Zurcher, F.; Togni, A. *J. Am. Chem. Soc.* 1997, 119, 10857–10858) but a catalyst that displays broad functional group tolerance, useful rates, and high turnover numbers for an intermolecular addition has been reported only recently. Specifically, the present inventors reported the addition of aromatic amines to both vinylarenes (Kawatsura, M.; Hartwig, J. F. *J. Am. Chem. Soc.* 2000, 122, 9546–9547) and dienes (Loeber, O.; Kawatsura, M.; Hartwig, J. F. *J. Am. Chem. Soc.* 2000, in press), and this chemistry included asymmetric additions.

The present inventors have also been interested in developing catalysts for the addition of amines to acrylic acid derivatives. Some of these reactions can be conducted in protic solvents under relatively mild conditions without a catalyst, but some cases do occur slowly, and most examples occur slowly in aprotic solvents. Thus, one could develop enantioselective additions of amines to acrylic acid derivatives if transition metal catalysts could be found for these transformations. The products of these additions would be β-amino acid derivatives that can be used in peptide analogs, or as precursors to optically active aminoalcohols, diamines, and lactams.

Lewis acids and bases catalyze the addition of azide and derivatives of hydroxylamine to substituted acrylates, and some of the catalysts provide nonracemic products in high enantiomeric excess (Sibi, M. P.; Shay, J. J.; Liu, M.; Jasperse, C. P. *J. Am. Chem. Soc.* 1998, 120, 6615–6616; Guerin, D. J.; Horstmann, T. E.; Miller, S. *J. Org. Lett.* 1999, 1, 1107; Myers, J. K.; Jacobsen, E. N. *J. Am. Chem. Soc.* 1999, 121, 8959). However, these catalysts are likely to be poisoned by alkyl- and arylamine reagents. Trogler reported the addition of anilinium salts to acrylonitrile catalyzed by palladium alkyl complexes ligated by either the PCP ligand $(t\text{-Bu})_2P(CH_2)_2CH(CH_2)_2P(t\text{-Bu})_2$ or the chelating phosphine $Me_2PCH_2CH_2PMe_2$.(Seligson, A. L.; Trogler, W. C. *Organometallics* 1993, 12, 744). However, this work did not extend successfully beyond acrylonitrile as Michael acceptor Accordingly, what is needed in the art is a facile method for addition of amines to carbon-carbon double bonds under mild conditions, and catalysts to catalyze such reactions. The present invention is believed to be an answer to that need.

SUMMARY OF THE INVENTION

In one aspect, the present invention is directed to a process for addition of amines to carbon-carbon double bonds in a substrate, comprising: reacting an amine compound comprising a primary or a secondary amine with a compound containing at least one carbon-carbon double bond in the presence a transition metal catalyst and in the absence of an alkylaluminum co-catalyst under reaction conditions effective to form a product having a covalent bond between the primary or secondary amine and the one carbon atom of the former carbon-carbon double bond; wherein the reaction time is less than 40 hours, and wherein the reaction produces more than 20 moles of product per mole of said transition metal in said catalyst and consumes more than 30% of either of the amine compound or the compound containing at least one carbon-carbon double bond, and wherein the product contains at least 80% of one regioisomer, the transition metal catalyst comprising a Group 8 metal and a ligand containing one or more 2-electron donor atoms.

In another aspect, the present invention is directed to a process for enantioselective addition of amines to carbon-carbon double bonds in a substrate, comprising: reacting an amine compound comprising a primary or a secondary amine with a compound containing at least one carbon-carbon double bond in the presence a chiral and nonracemic transition metal catalyst under reaction conditions effective to form a product having a covalent bond between the primary or secondary amine and one carbon atom of the former carbon-carbon double bond; the transition metal catalyst comprising a Group 8 metal and a ligand containing one or more 2-electron donor atoms; and wherein the product is formed in greater than 20% yield, and with greater than 50% enantioselectivity.

In yet another aspect, the present invention is directed to a method for determining the activity of a catalyst useful in a reaction that adds primary or secondary amine compounds to compounds containing at least one carbon-carbon double bond, comprising: (1) reacting in a reaction vessel an amine compound comprising a primary or a secondary amine with a compound containing at least one carbon-carbon double bond in the presence a transition metal catalyst under reaction conditions effective to form a product containing a covalent bond between the primary or secondary amine and one carbon atom of the former carbon-carbon double bond, the transition metal catalyst comprising a Group 8 metal and a ligand containing one or more 2-electron donor atoms; (2) adding a calorimetric agent to the reaction vessel, the calorimetric agent reactive with the amine compound or the product; and (3) evaluating the degree of color in the reaction vessel to determine the activity of the catalyst.

These and other aspects will become apparent upon reading the following detailed description of the invention.

BRIEF DESCRIPTION OF THE FIGURES

The invention will be more fully understood from the following detailed description taken in conjunction with the accompanying drawings in which.

DETAILED DESCRIPTION OF THE INVENTION

Figure 1:
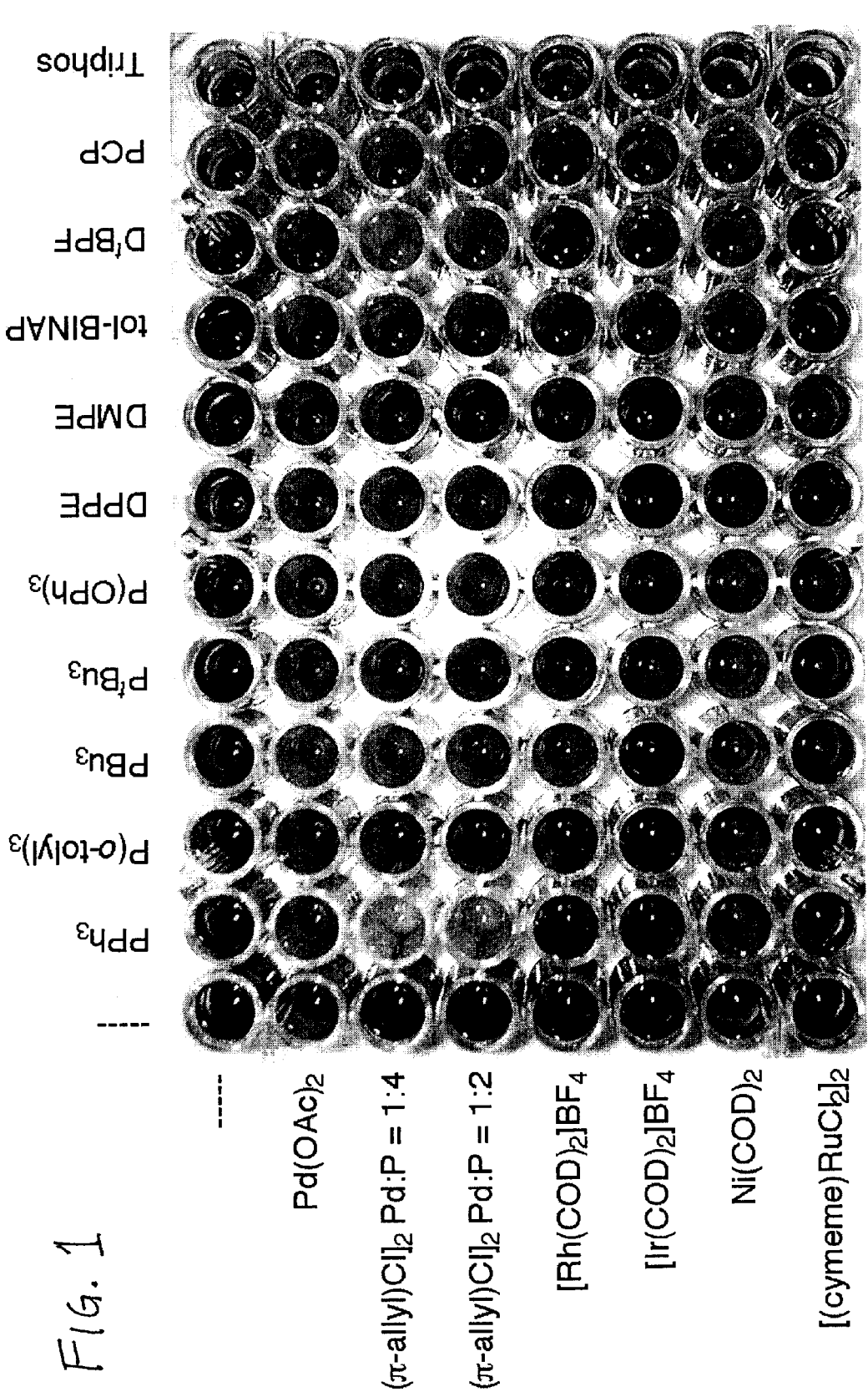
FIG. 1 shows the results of high throughput analysis of transition metal catalysts that are potentially useful in the addition of aniline to 1,3-cyclohexadiene.

It now has been surprisingly found, in accordance with the present invention, that a solution is provided to the problem of providing a general and efficient process for the addition of amines to carbon-carbon double bonds under mild conditions. The present inventors have solved this problem by utilizing reaction conditions that include a transition metal catalyst having a Group 8 metal and at least one ligand containing one or more 2-electron donor atoms. In one embodiment, the catalyst is represented by the formula:

$$(L)^1_{1-6}(L)^2_{1-6}MX_y$$

wherein $(L)^1$ and $(L)^2$ are the ligands containing two-electron donor atoms, M is the Group 8 transition metal, each X is independently a monovalent anionic ligand, including for example a halide, such as chloride or bromide; a carboxylate, such as acetate or trifluoroacetate; or an alkyl sulfonate, such as triflate; or X is a divalent anionic ligand, such as sulfonate or carbonate; and wherein y represents the total number of anionic ligands X required to balance charge, typically from 0 to about 4. Preferably, the ligand is selected from unsaturated Group 15 heterocycles, Group 15-substituted metallocenes, Group 15-substituted alkanes, Group 15-substituted arylenes, and combinations thereof. In one preferred embodiment, the catalyst comprises a palladium complex of 1,1'-bis(diphenylphosphino)-2,2'-binapthyl (BINAP), or 1,1'-bis(diphenylphosphino) ferrocene (DPPF). The process of the present invention provides a general process for addition of amines to carbon-carbon double bonds to form products that are particularly significant in the development of pharmacologically active compounds and production of polymers and oligomers.

As mentioned above, the present invention is directed to a process for the addition of amines to carbon-carbon double bonds in a substrate. The process involves reacting an amine compound comprising a primary or a secondary amine with a compound containing at least one carbon-carbon double bond in the presence a transition metal catalyst and in the absence of an alkylaluminum co-catalyst, and under reaction conditions effective to form a covalent bond between the amine and a carbon atom of the former carbon-carbon double bond. The transition metal catalyst comprises a Group 8 metal and a ligand containing one or more 2-electron donor atoms. The reaction time is typically less than 40 hours, and the reaction produces more than 20 moles of product per mole of said transition metal in said catalyst, and consumes more than 30% of either of the starting reactants. Further, the reaction product contains at least 80% of one regioisomer.

As defined herein, the term "regioisomers" refers to two or more isomeric products in which the nitrogen is not located at the same carbon of the product. Alternatively, for reactions of dienes, regioisomers may contain the nitrogen bound to the same carbon but the remaining double bond not connecting the same two carbons.

As defined herein, the term "regioselective" refers to a process that generates unequal quantities of two enantiomeric products.

As defined herein, the term "enantioselective" refers to a process, catalyst, or reagent that generates unequal quantities of two enantiomeric products.

More specifically, the process of the present invention may be represented as shown in Eqn. 1:

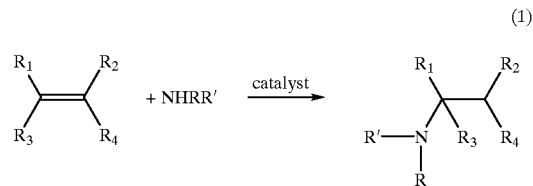

(1)

Briefly, in Eqn. 1, a primary or a secondary amine compound is reacted with a substrate compound possessing a double bond and in the presence of a catalyst to form a structure wherein the double bond has been reduced to a single bond, and a new covalent bond is formed between the nitrogen atom of the amine compound and a carbon atom that formed part of the double bond structure of the substrate. In Eqn. 1, $R_1$, $R_2$, $R_3$, $R_4$ may be hydrogen, or another group such as alkyl, aryl, and the like, and as explained in more detail below. R and R' may be hydrogen or an alkyl or aryl group. Furthermore, R and R' may be joined to form a cyclic structure. Each of these components is explained in more detail below.

The amine compound used in the method of the present invention may be any primary or a secondary amine. Exemplary primary and secondary amines include aryl amines, cyclic amines, alkylamines, carbamates, and combinations thereof. Useful aryl amines include, but are not limited to, substituted or unsubstituted aniline, substituted or unsubstituted aminonaphthalene, substituted or unsubstituted anisidine, substituted or unsubstituted toluidine, and combinations thereof. Useful cyclic amines include piperidine, morpholine, pyrrolidine, aziridine, azetidine, hexamethylene imine, and combinations thereof.

Examples of compounds containing at least one carbon-carbon double bond that are useful in the method of the present invention include vinylarenes, cyclic 1,3-dienes, acyclic 1,3-dienes, acrylates, acrylonitriles, and combinations thereof. Useful vinylarenes include substituted or unsubstituted styrenes, and substituted or unsubstituted vinylnaphthalenes. Useful cyclic 1,3-dienes include 1,3-cyclohexadiene, 1,3-cycloheptadiene, and 1,3-cyclooctadiene. Useful acyclic dienes include 2,3-dimethylbutadiene and isoprene. Examples of useful acrylates include acrylic acid esters, methylacrylonitrile, and crotonitrile. Suitable combinations of any or all of the above compounds may also suitably be used in the method of the present invention.

The method of the present invention may optionally include an acid. Suitable acids include trifluoroacetic acid (TFA), trifilic acid, benzoic acid, acetic acid, methane sulfonic acid, phenylsulfonic acid, pentafluorobenzoic acid, and the like.

As mentioned above, the transition metal catalyst employed in the method of the present invention comprises a Group 8 metal and a ligand containing one or more 2-electron donor atoms. The Group 8 transition metal atom or ion is preferably selected from iron, cobalt, nickel, ruthenium, rhodium, palladium, osmium, iridium, and platinum. More preferably, the Group 8 metal is palladium, platinum, or nickel, and most preferably, palladium. The Group 8 metal may exist in any oxidation state ranging from the zero-valent state to any higher variance available to the metal.

The ligand portion of the catalyst may be a neutral molecule or charged ion and may be monodentate or chelating. A monodentate ligand contains an element bearing a nonbinding electron pair (E) when E is not bonded to the metal, and one to four substituents R that are bonded to E through a carbon, nitrogen, oxygen, or sulfur atom. A chelating ligand possesses a plurality of such elements bearing a nonbinding electron pair (E).

Preferably, the ligand contains at least one element from Group 15 (formerly Known as Group VB) of the Periodic Table, preferably, at least one element of nitrogen, phosphorus, or arsenic, and more preferably nitrogen or phosphorus. More specifically, the ligand is selected from the group consisting of Group 15-substituted arylenes, Group 15-substituted metallocenes, unsaturated Group 15 heterocycles, and Group 15-substituted alkanes.

The term "Group 15-substituted arylenes" as used herein includes aromatic compounds substituted with at least one Group 15-containing moiety, preferably, at least one dialkyl or diaryl Group 15 moiety or hybrid thereof. The aromatic compound can be a single ring, fused ring, or multiple ring assembly. Other chelating elements, such as oxygen or sulfur, may be present. Non-limiting examples of Group 15-substituted arylenes which are chelating and beneficially employed in the process of this invention include 1,2-bis(diphenylphosphino)benzene, 1,1'-bis(diphenylphosphino)-2,2'-binaphthyl, 1-(dimethylarsino)-2-bis[(dimethylamino)phosphino)]benzene, 1,2-bis(dimethylarsino)benzene, 5-10-dihydro-5,10-diphenyl-5-phospha-10-arsa-anthracene, 2-diphenylphosphino-N,N-dimethylaniline, 1,8-bis(diphenylphosphino)naphthalene, 2,2-bis(diphenylphosphino)diphenyl ether, 4,5-bis(diphenylphosphino)-9,9-dimethyl)xanthene, and 1,1'-bis(di-p-tolylphosphino)-2,2'-binaphthyl, 1-diphenylphosphino-1'-dimethylamino-2,2'-binaphthyl, 1-dicyclohexylphosphino-1'-dimethylamino-2,2'-binaphthyl, 1-di-t-butylphosphino-1'-dimethylamino-2,2'-binaphthyl, 1-di-i-propylphosphino-1'-dimethylamino-2,2'-binaphthyl, 1-diphenylphosphino-1'-methoxy-2,2'-binaphthyl, 1-dicyclohexylphosphino-1'-methoxy-2,2'-binaphthyl, 1-di-t-butylphosphino-1'-methoxy-2,2'-binaphthyl, 1-di-i-propylphosphino-1'-dimethylamino-2,2'-binaphthyl, 1-diphenylphoesphino-1'-dimethylamino-2,2'-biphenyl, 1-dicyclohexylphosphino-1'-dimethylamino-2,2'-biphenyl, 1-di-t-butylphosphino-1'-dimethylamino-2,2'-biphenyl, 1-di-i-propylphosphino-1'-dimethylamino-2,2'-binaphthyl, 1-diphenylphosphino-1'-methoxy-2,2'-biphenyl, 1-dicyclohexylphosphino-1'-methoxy-2,2'-biphenyl, 1-di-t-butylphosphino-1'-methoxy-2,2'-biphenyl, and 1-di-i-propylphosphino-1'-dimethylamino-2,2'-binaphthyl. Analogous diamino, diphosphino, and diarsino compounds and hybrids thereof are also suitable. Preferably, the Group 15-substituted arylene is a Group 15-substituted $C_{4-20}$ arylene, more preferably, a Group 15-substituted binaphthyl compound, more preferably, 1,1'-bis(diphenylphosphino)-2,2'-binaphthyl (BINAP) or 1,1'-bis(di-p-tolyl-phosphino)-2,2'-binaphthyl.

The term "Group 15-substituted metallocenes" as used herein includes metallocenes which are substituted with at least one Group 15-containing moiety, preferably at least one dialkyl or diaryl Group 15 moiety or hybrid thereof. Other chelating elements, for example, oxygen or sulfur, may be present. The metallocene itself comprises a transition metal atom or ion which is bonded to one or more $C_{4-8}$ multiply unsaturated hydrocarbon ring compounds. Suitable non-limiting examples of transition metal atoms in the metallocene include iron, titanium, vanadium, chromium, manganese, cobalt, nickel, molybdenum, and ruthenium. Preferably, the transition metal atom in the metallocene is iron. The $C_{4-8}$ multiply unsaturated hydrocarbon ring compounds suitably include cyclobutadiene, cyclopentadienyl, benzene, cycloheptatrienyl, and cyclooctatetraene. Representative metallocenes include ferrocene, ruthenocene, bis(benzene)chromium, bis(benzene)-molybdenum, bis(benzene)tungsten, and cobaltocenium. Non-limiting examples of ligands which classify as chelating Group 15-substituted metallocenes include 1,1'bis(diphenylphosphino)ferrocene, 1,1'-bis(di-o-tolylphosphino)ferrocene (DTPF), 1-diphenylphosphino-2-(1-dimethylamino)ethyl ferrocene, 1-diphenylarsino-1'-diphenyl-phosphino ferrocene, 1-diphenylphosphino-2-(1-diphenylphosphino) ethyl ferrocene, 1-diphenylphosphino-2-(1-di-t-butylphosphino)ethyl ferrocene, 1-diphenylphosphino-2-(1-dicyclohexylphosphino)ethyl ferrocene, 1-dicyclohexylphosphino-2-(1-diphenylphosphino)ethyl ferrocene, 1-dicyclohexylphosphino-2-(1-dicyclohexylphosphino) ethyl ferrocene, 1-dicyclohexylphosphino-2-(1-dimethylamino)ethyl ferrocene, 1-di-t-butylphosphino-2-(1-dimethylamino)ethyl ferrocene, 1-di-i-propylphosphino-2-(1-dimethylamino)ethyl ferrocene, 1-diphenylphosphino-2-(1-dimethylamino)ethyl ferrocene, 1-[2-(diphenylphosphino) ferroceny]ethyl methyl ether, 1-[2-(dicyclohexylphosphino)ferrocenyl]ethyl methyl ether, 1-[2-(di-i-propylphosphino)ferrocenyl]ethyl methyl ether, and 1-[2-(di-t-butylphosphino)ferrocenyl]ethyl methyl ether. Analogous phosphine and amine substituted derivatives of the aforementioned metallocenes may also be employed. Preferably, the Group 15-substituted metallocene is a Group 15-substituted ferrocene, more preferably, 1,1'-bis(diphenylphosphino)ferrocene (DPPF).

The term "unsaturated Group 15 heterocycles" as used herein includes any unsaturated single ring, multiple ring assembly, or fused ring system which comprises at least one Group 15 heteroatom. Preferably, the heteroatom is nitrogen. Chelating atoms outside of Group 15, such as oxygen or sulfur, may also be present. Non-limiting examples of unsaturated Group 15 heterocycles which can be beneficially employed in the process of the present invention include bipyridine, alkoxypyridine, imidazole, pyrazole, pyrimidine, pyridazine, purine, and quinazoline. Preferably, the unsaturated Group 15 heterocycle is an unsaturated $C_{5-15}$ Group 15 heterocycle, more preferably bipyridine or alkoxypyridine.

The term "Group 15-substituted alkanes" as used herein includes alkanes, preferably $C_{2-5}$ alkanes, and more preferably $C_{3-4}$ alkanes, which are substituted with at least one Group 15-containing moiety, preferably, a dialkyl or diaryl Group 15 moiety or hybrid thereof. Non-limiting examples of ligands which classify as chelating Group 15-substituted alkanes and which may be beneficially employed in the process of the present invention include 1,3-bis (diphenylphosphino)propane, 1,4-bis(diphenylphosphino) butane, 1,3-bis(diphenylarsino)propane, 1,4-bis (diphenylarsino)butane, 1-(diphenylphsophine)-2-(N,N-dimethyl)ethane, 1-(diphenyphosphino)-3-(N,N-dimethyl) propane, and 1-(diphenylarsino)-2-(diphenylphosphino) ethane. One particularly useful example is 1,4-bis (diphenylphosphino)butane.

In one preferred embodiment, the ligand is a bidentate ligand containing at least one phosphorous atom. More preferably, the ligand is a bidentate ligand selected from the group consisting of phosphorous-substituted arylenes and phosphorous-substituted metallocenes. Most preferably, the ligand is 1,1'-bis(diphenylphosphino)-2,2'-binapthyl (BINAP), 1,1'-bis(di-p-tolyphosphino)-2,2'-binapthyl(Tol-BINAP), or 1,1'-bis(diphenylphosphino)ferrocene (DPPF).

In a second preferred embodiment, the ligand is a monodentate ligand containing one phosphorus atom. More preferably, the ligand is a monophosphine containing an aryl group. More preferably, the ligand is a monophosphine selected from the group consisting of triphenylphosphine, and substituted triarylphosphines.

Many of the aforementioned metal catalysts which are beneficially employed in the process of this invention can be represented by the following formula:

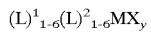

wherein $(L)^1$ and $(L)^2$ are the ligands containing two-electron donor atoms, M is the Group 8 transition metal, each X is independently a monovalent anionic ligand, including for example a halide, such as chloride or bromide; a carboxylate, such as acetate or trifluoroacetate; or an alkyl sulfonate, such as triflate; or X is a divalent anionic ligand, such as sulfonate or carbonate; and wherein y represents the total number of anionic ligands X required to balance charge, typically from 0 to about 4. It is to be understood that any of the ligands described earlier may be used in the above formula. Non-limiting examples of suitable transition metal complexes include [1,1'-bis(diphenylphosphino)ferrocene] palladium (II) bis-triflate, [1,1'-bis(diphenylphosphino) ferrocene]palladium (II) bis-trifluoroacetate, [1,1'-bis (diphenylphosphino)ferrocene]palladium (II) bis-tosylate, [1,1'-bis(diphenylphosphino)binaphthyl]palladium (II) bis-triflate, [1,1'-bis(diphenylphosphino)binaphthyl]palladium (II) bis-trifluoroacetate, [1,1'-bis(diphenylphosphino) binaphthyl]palladium (II) bis-tosylate, bis (triphenylphosphine)palladium (II) bis-triflate, bis (triphenylphosphine)palladium (II) bis-trifluoroacetate, bis (triphenylphosphine)palladium (II) bis-tosylate, tetrakis (triphenylphosphine)Palladium(0), bis[1,1'-bis (diphenylphosphino)ferrocene]palladium(0) and bis[1,1-bis (diphenylphosphino)binaphthyl]palladium(0) and analogous complexes containing bidentate ligands mentioned hereinbefore with iron, cobalt, nickel, ruthenium, rhodium, osmium, and iridium as the metal component.

Methods for preparing the aforementioned catalysts are known to those skilled in the art. For a description of general synthetic techniques, see Inorganic Synthesis: Reagents for Transition Metal Complex and Organometallic Systems; R. J. Angelici, Ed., Wiley-Interscience: New York, 1990, Vol. 28, pp. 77–135 (Chapter 2), incorporated herein by reference, wherein representative preparations of Group 8 complexes containing chelating amine, phosphine, and arsine ligands are taught.

Alternatively, the catalyst can be prepared in situ in the hydroamination reaction mixture. If the latter mixture is employed, then a Group 8 catalyst precursor compound and the desired ligand are independently added to the reaction mixture wherein formation of the transition metal catalyst occurs in situ. Suitable precursor compounds include alkene and diene ABE complexes of the Group 8 metals, preferably, allylmetal halide or trifluoroacetate complexes of the Group 8 metals, as well as, monodentate phosphine complexes of the Group 8 metals, and Group 8 carboxylates or sulfonates. In the presence of the ligand, such as $PPh_3$, DPPF or BINAP, in situ formation of the transition metal catalyst occurs. Non-limiting examples of suitable compounds include [bis-(dibenzylidene)acetone]palladium (0), tetrakis-(triphenylphosphine)-palladium (0), tris-[(dibenzylidene) acetone]palladium (0), tris-[(dibenzylidene) acetone] dipalladium (0), palladium (II) acetate, and palladium (II) trifluoroacetate, (allyl)palladium chloride dimer, bis (cyclooctadiene)Ni(0), and the analogous complexes of iron, cobalt, ruthenium, rhodium, osmium, iridium, and platinum. Any of the aforementioned catalyst precursors may include a solvent of crystallization. Group 8 metals supported on carbon, preferably, palladium on carbon, can also be suitably employed as a precursor compound. Preferably, the catalyst precursor compound is palladium (II) trifluoroacetate or bis(cyclooctadiene)Ni(0). It should be noted that The phrase "moles of product per mole of catalyst", when referring to an in situ generation of catalyst, refers to the moles of metal in the catalyst.

As an alternative embodiment of this invention, the catalyst may be anchored or supported on a catalyst support, including a refractory oxide, such as silica, alumina, titania, or magnesia; or an aluminosilicate clay, or molecular sieve or zeolite; or an organic polymeric resin.

Heretofore, the transition metal catalyst has been described as comprising a transition metal and a ligand. It is not precisely known, however, whether both, one, or neither donor atoms of the ligand are bound to the transition metal during the entire process of this invention and, if a chelating ligand is used, whether the chelating ligand is in a labile or non-bonded configuration relative to the transition metal during part or all of the process. Generally, it is believed that the ligand is bonded through the Group 15 element to the transition metal; however, such a theory should not be binding upon the invention in any manner. Modern analytical techniques, such as nuclear magnetic resonance spectroscopy ($^{13}C$, $^1H$, $^{31}P$), infrared and Raman spectroscopies, and X-ray diffraction, may assist in the determination of initial catalyst structure and changes in structure throughout the process.

The quantity of transition metal catalyst which is employed in the process of this invention is any quantity which promotes the formation of the product, generally up to about 5 mol %. Generally, the quantity is a catalytic amount, which means that the catalyst is used in an amount which is less than stoichiometric relative to the unsaturated organic sulfonate. Preferably, the transition metal catalyst ranges from about 0.1 to about 5 mole percent, and more preferably from about 1 to about 5 mole percent, based on the amount of amine compound or the compound with a carbon-carbon double bond.

The process described herein may be conducted in any conventional reactor designed for catalytic processes. However, the reaction should take place in the absence of any alkylaluminum co-catalysts. Continuous, semi-continuous, and batch reactors can be employed. If the catalyst is substantially dissolved in the reaction mixture as in homogeneous processes, then batch reactors, including stirred tank and pressurized autoclaves, can be employed. If the catalyst is anchored to a support and is substantially in a heterogeneous phase, then fixed-bed and fluidized bed reactors can be used. In the typical practice of this invention the reactants and catalyst are mixed in batch, optionally with a solvent, and the resulting mixture is maintained at a temperature and pressure effective to prepare the product.

Any solvent can be used in the process of the invention provided that it does not interfere with the formation of the product. Both aprotic and protic solvents and combinations thereof are acceptable. Suitable aprotic solvents include, but are not limited to, aromatic hydrocarbons, such as toluene and xylene, chlorinated aromatic hydrocarbons, such as dichlorobenzene, and ethers, such as tetrahydrofuran. Suitable protic solvents include, but are not limited to, water and aliphatic alcohols, such as ethanol, isopropanol, and cyclohexonol, as well as glycols and other polyols. The amount of solvent which is employed may be any amount, preferably an amount sufficient to solubilize, at least in part, the reactants and base. A suitable quantity of solvent typically ranges from about 1 to about 100 grams solvent per gram reactants. Other quantities of Solvent may also be suitable, as determined by the specific process conditions and by the skilled artisan. The process of the invention may also be conducted without any solvent.

Generally, the reactants may be mixed together or added to a solvent in any order. Air is preferably removed from the reaction vessel during the course of the reaction, however this step is not always necessary. If it is desirable or necessary to remove air, the solvent and reaction mixture can be sparged with a non-reactive gas, such as nitrogen, helium, or argon, or the reaction may be conducted under anaerobic conditions. The process conditions can be any operable conditions which yield the desired product. Beneficially, the reaction conditions for this process are mild. For example, a preferred temperature for the process of the present invention ranges from about ambient, taken as about 22° C., to about 150° C., and preferably, from about 25° C. to about 110° C. The process may be run above or below atmospheric pressures if necessary, but typically proceeds sufficiently well at about atmospheric pressure. The process is generally run for a time sufficient to convert as much of the starting materials to product as possible. The reaction time is less than 40 hours (typically between about 30 minutes and 24 hours), and the reaction generally produces more than 20 moles of product per mole of catalyst and consumes more than 30% of either of the starting reactants. Further, the reaction product contains at least 80% of one regioisomer.

The product can be recovered by conventional methods known to those skilled in the art, including, for example, distillation, crystallization, sublimation, and gel chromatography. The yield of product will vary depending upon the specific catalyst, reagents, and process conditions used. For the purposes of this invention, "yield" is defined as the mole percentage of product recovered, based on the number of moles of primary or secondary amine compound employed, or on the number of moles of substrate with a carbon-carbon double bond. Typically, the yield of product is greater than about 30 mole percent. Preferably, the yield of product is greater than about 60 mole percent, and more preferably, greater than about 80 mole percent.

According to another embodiment of the process of the present invention, it is possible to perform enantioselective additions of amines to compound containing carbon-carbon double bonds. As explained more fully in the following Examples, selection and use of a chiral and nonracemic catalyst for use in the method of the present invention results in enantioselectivity (e.g., nonracemic) product. Such chiral and nonracemic catalysts may be assembled using ligands purchased from the usual commercial sources and employed in the method of the invention directly. Alternatively, it is possible to synthesize the desired ligand in nonracemic form or racemic form, followed by separation of the racemic mixture into separate enantiomers using methods well known in the art.

Using chiral catalysts as described above, reaction of aniline with 4-trifluoromethylstyrene catalyzed by ((R)-BINAP)Pd(OSO$_2$CF$_3$)$_2$ at 25° C. gave the addition product in 81% yield and 81% enantioselectivity. In another example, 5 mol % (Pd(allyl)Cl)$_2$ and 11 mol % of Trost's ligand (Ligand 1) (Trost, B. M. et al., Angew. Chem. Int. Ed. Engl. 1996, 35, 99–102)

Ligand 1

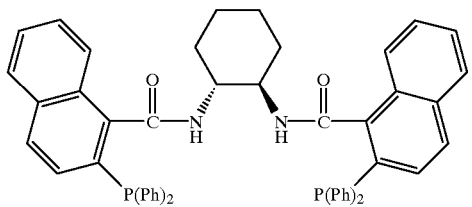

at 1.25 mM in THP solvent at room temperature provided high combinations of yield and enantioselectivity for a broad range of aryl amines and 1,3 cyclohexanedienes (See Examples 31–42). Thus, one may perform asymmetric transformations using the method of the present invention.

To evaluate simultaneously a large number of potential catalysts for the use in the process of the present invention, a colorimetric method was developed to monitor the presence or absence of amine compounds such as anilines. Briefly, this colorimetric method involves reacting an amine compound and a compound containing at least one carbon-carbon double bond in a reaction vessel, and in the presence of a transition metal catalyst under test. As described above, the carbon-carbon double bond is reduced, and a new single bond is formed between one of the carbons in the former carbon-carbon double bond and the nitrogen of the amine group. Typically, the transition metal catalyst under test contains a Group 8 metal and a ligand containing one or more 2-electron donor atoms. A calorimetric agent is then added to the reaction vessel, and is typically reactive with the amine compound or the product. The degree of color in the reaction vessel is then evaluated to determine the activity of the catalyst. As will be appreciated, it is possible to monitor calorimetrically either the consumption of reactants (e.g., aniline), or the production of product using the calorimetric assay.

One useful calorimetric reagent is 2-furaldehyde and acetic acid. Furfural undergoes a condensation and ring opening with two equivalents of aniline, but not the alkyl, benzylic or allylic amine product, in the presence of acid to create a red product. Thus, addition of furfural and acid to catalytic reactions of aromatic amines will reveal which catalysts are most active; reactions that consume the largest amount of aniline will show the least red color.

Another useful calorimetric reagent is sodium nitroferricyanide(III) dihydrate (Na$_2$Fe(CN)$_5$NO.2H$_2$O) and acetaldehyde. Basic solutions of sodium nitroferricyanide dihydrate and acetaldehyde become blue in the presence of secondary alkylamines. The degree of blue color can be used to evaluate the amount of secondary amine present in the reaction. In one embodiment, this calorimetric reagent will allow one to monitor the consumption of secondary alkylamines reagents. In another case, the calorimetric reagent will allow one to monitor the formation of secondary amine products.

EXAMPLES

The following examples are intended to illustrate, but in no way limit the scope of the present invention. All parts and percentages are by weight. Percentages such as yield are by mole quantities. All temperatures are in degrees Celsius unless explicitly stated otherwise.

General Methods. Reactions were conducted using standard Schlenk and drybox techniques. $^1H$, $^{13}C\{^1H\}$, and $^{19}F\{^1H\}$ NMR spectra were recorded on Bruker AM 400 and AM 500 MHz spectrometers using deuterated or residual protiated solvent ($^1H$, $^{13}C$) or external $CFCl_3$ ($^{19}F$) as a reference; resonances downfield to the standard are reported as positive. Low resolution mass spectra were obtained on a Hewlett Packard 5890 series II gas chromatograph interfaced with a Hewlett Packard 5989A mass spectrometer. IR spectra were recorded on a MIDAC FTIR spectrometer. Toluene and THF were distilled from sodium and benzophenone and were stored in the drybox. All other chemicals were purchased from commercial sources and used as received.

Examples 1–14

Palladium Catalyzed Hydroamination of Vinylarenes using Arylamines. Fourteen Examples of palladium-catalyzed hydroamination of vinylarenes with arylamines are shown in Table 2 (Entries 1–14). A representative procedure is the production of N-Phenyl-N-(1-phenylethyl) amine. $Pd(OCOCF_3)_2$ (6.6 mg, 0.020 mmol) and DPPF were suspended in 0.5 mL of toluene in a screw-capped vial. The vial was sealed with a cap containing a PTFE septum and removed from the drybox. Styrene (156 mg, 1.5 mmol), aniline (93 mg, 1.0 mmol) and $CF_3CO_2H$ (30 mg, 0.20 mmol) were added to the reaction mixture by syringe. The reaction mixture was stirred at 100° C. for 12 h. The reaction mixture was adsorbed onto silica gel and isolated by eluting with 10% ethyl acetate/hexanes to give 197 mg (100%) of N-Phenyl-N-(1-phenylethyl)amine. Additional products were made similarly and were analyzed as follows.

N-Phenyl-N-(1-phenylethyl)amine: $^1H$ NMR: ($CDCl_3$) δ 7.39 (d, J=7.3 Hz, 2H), 7.33 (t, J=7.3 Hz, 2H), 7.25 (t, J=7.3 Hz, 1H), 7.11 (t, J=7.3 Hz, 2H), 6.67 (t, J=7.3 Hz, 1H), 6.54 (d, J=7.3 Hz, 2H), 4.50 (q, J=6.8 Hz, 1H), 4.15 (brs, 1H), 1.53 (d, J=6.8 Hz, 3H). $^{13}C\{^1H\}$ NMR: ($CDCl_3$) δ 147.36, 145.30, 129.17, 128.70, 126.93, 125.92, 117.34, 113.41, 53.53, 25.03.

N-[1-(2-naphthyl)ethyl]-N-phenylamine: 99% yield, eluted from silica gel using 90/10 hexanes/ethyl acetate. $^1H$ NMR: ($CDCl_3$) δ 7.85–7.81 (m, 4H), 7.53 (d, J=9.0 Hz, 1H), 7.48–7.45 (m, 2H), 7.10 (t, J=7.7 Hz, 2H), 6.66 (t, J=7.7 Hz, 1H), 6.58 (d, J=7.7 Hz, 2H), 4.66 (q, J=6.7 Hz, 1H), 4.18 (brs, 1H), 1.61 (d, J=6.7 Hz, 3H). $^{13}C\{^1H\}$ NMR: ($CDCl_3$) δ 146.01, 141.53, 132.33, 131.49, 127.89, 127.25, 126.60, 126.44, 124.77, 124.66, 124.51, 124.27, 116.01, 112.12, 52.49, 23.86.

N-(4-methoxyphenyl)-N-(1-phenylethyl)amine: 93% yield, eluted from silica gel using 90/10 hexanes/ethyl acetate. $^1H$ NMR: ($CDCl_3$) δ 7.30–7.22 (m, 4H), 7.18–7.13 (t, J=6.8 Hz, 1H), 6.61 (d, J=8.8 Hz, 2H), 6.40 (d, J=8.8 Hz, 2H), 4.33 (q, J=6.8 Hz, 1H), 3.62 (s, 3H), 1.42 (d, J=6.8 Hz, 3H). $^{13}C\{^1H\}$ NMR: ($CDCl_3$) δ 152.28, 145.85, 141.91, 129.02, 127.23, 126.29, 115.13, 114.95, 56.13, 54.67, 25.55.

N-(1-phenylethyl)-N-[4-(trifluoromethyl)phenyl]amine: 64% yield, eluted from silica gel using 90/10 hexanes/ethyl acetate. $^1H$ NMR: ($CDCl_3$) δ 7.21–7.22 (m, 6H), 7.19–7.16 (m, 1H), 6.42 (d, J=8.8 Hz, 2H), 4.43 (q, J=6.8 Hz, 1H), 3.34–4.22 (brs, 1H), 1.45 (d, J=6.8 Hz, 3H). $^{13}C\{^1H\}$ NMR: ($CDCl_3$) δ 149.97, 144.63, 129.23, 127.61, 126.93, 126.71, 126.10, 126.86 (q, $J_{C-F}$=4.1 Hz), 112.84, 53.62, 23.62. Anal. Calcd for $C_{15}H_{14}NF_3$: C, 67.92; H, 5.32; N, 5.28. Found: C, 67.79; H, 5.22; N, 5.58.

N-methyl-N-phenyl-N-(1-phenylethyl)amine: 65% yield, eluted from silica gel using 95/5 hexanes/ethyl acetate. $^1H$ NMR: ($CDCl_3$) δ 7.27–7.23 (m, 3H), 7.20–7.25 (m, 4H), 6.76 (d, J=8.8 Hz, 2H), 6.65 (t, J=7.6 Hz, 1H), 5.05 (q, J=6.8 Hz, 1H), 2.60 (s, 3H), 1.41 (d, J=6.8 Hz, 3H). $^{13}C\{^1H\}$ NMR: ($CDCl_3$) δ 150.28, 142.89, 129.28, 128.45, 126.98, 126.89, 116.70, 113.11, 56.57, 31.92, 16.40.

N-(2-methylphenyl)-N-(1-phenylethyl)amine: 71% yield, eluted from silica gel using 95/5 hexanes/ethyl acetate. $^1H$ NMR: ($CDCl_3$) δ 7.30–7.22 (m, 4H), 7.14 (t, J=7.2 Hz, 1H), 6.96 (d, J=7.2 Hz, 1H), 6.88 (t, J=7.2 Hz, 1H), 6.52 (t, J=7.2 Hz, 1H), 6.28 (d, J=7.2 Hz, 1H), 4.45 (q, J=6.8 Hz, 1H), 3.83–3.75 (brs, 1H), 2.15 (s, 3H), 1.48 (d, J=6.8 Hz, 3H). $^{13}C\{^1H\}$ NMR: ($CDCl_3$) δ 145.03, 129.74, 128.42, 128.20, 126.77, 126.62, 125.56, 121.32, 116.58, 110.78, 53.07, 25.06, 17.43.

N-(1-naphthyl)-N-(1-phenylethyl)amine: 94% yield, eluted from silica gel using 95/5 hexanes/ethyl acetate. $^1H$ NMR: ($CDCl_3$) δ 7.86–7.82 (m, 1H), 7.71–7.67 (m, 1H), 7.41–7.32 (m, 4H), 7.23 (t, J=7.6 Hz, 2H), 7.17–7.12 (m, 1H), 7.11–7.08 (m, 2H), 6.31–6.26 (m, 1H), 4.70–4.60 (brs, 1H), 4.58 (q, J=6.8 Hz, 1H), 1.56 (d, J=6.8 Hz, 3H). $^{13}C\{^1H\}$ NMR: ($CDCl_3$) δ 145.62, 142.80, 134.98, 129.49, 129.42, 127.69, 127.29, 126.53, 126.37, 125.41, 123.93, 120.49, 117.93, 106.71, 54.28, 26.00. Anal. Calcd for $C_{18}H_{17}N$: C, 87.41; H, 6.93; N, 5.66. Found: C, 87.30; H, 6.85; N, 5.53.

N-methyl-N-[1-(2-naphthyl)ethyl]-N-phenylamine: 74% yield, eluted from silica gel using 95/5 hexanes/ethyl acetate. $^1H$ NMR: ($CDCl_3$) δ 7.72–7.69 (m, 4H), 7.40 (d, J=8.8 Hz, 1H), 7.38–7.31 (m, 2H), 7.01–6.96 (m, 2H), 6.54 (t, J=8.0 Hz, 1H), 6.45 (d, J=9.6 Hz, 2H), 4.53 (q, J=6.8 Hz, 1H), 4.20–3.90 (brs, 1H), 1.47 (d, J=6.8 Hz, 3H). $^{13}C\{^1H\}$ NMR: ($CDCl_3$) δ 148.24, 143.72, 134.54, 133.71, 130.11, 129.46, 128.81, 128.65, 126.99, 126.49, 125.39, 125.23, 118.32, 114.37, 54.71, 26.04. Anal. Calcd for $C_{19}H_{19}N$: C, 87.31; H, 7.33; N, 5.36. Found: C, 87.41; H, 7.24; N, 5.31.

N-phenyl-N-{1-[4-(trifluoromethyl)phenyl]ethyl}amine: 99% yield, eluted from silica gel using 90/10 hexanes/ethyl acetate. $^1H$ NMR: ($CDCl_3$) δ 7.49, (d, J=8.0 Hz, 2H), 7.40 (d, J=8.0 Hz, 2H), 7.05–6.99 (m, 2H), 6.59 (t, J=7.6 Hz, 1H), 6.39 (d, J=7.6 Hz, 2H), 4.44 (q, J=6.8 Hz, 1H), 4.05–3.90 (brs, 1H), 1.44 (d, J=6.8 Hz, 3H). $^{13}C\{^1H\}$ NMR: ($CDCl_3$) δ 148.74, 146.05, 128.45, 125.39, 124.90 (q, $J_{C-F}$=4.2 Hz), 124.84, 122.15, 116.93, 112.54, 52.55, 24.35. Anal. Calcd for $C_{15}H_{14}NF_3$: C, 67.92; H, 5.32; N, 5.28. Found: C, 68.20; H, 5.38; N, 5.19.

N1-(2,5-dimethylphenyl)ethyl]-N-phenylamine: 94% yield, eluted from silica gel using 95/5 hexanes/ethyl acetate. $^1H$ NMR: ($CDCl_3$) δ 7.16 (s, 1H), 7.04–6.97 (m, 3H), 6.87 (d, J=7.6 Hz, 1H), 6.56 (t, J=7.6 Hz, 1H), 6.38 (d, J=7.6 Hz, 2H), 4.55 (q, J=6.8 Hz, 1H), 4.00–3.80 (brs, 1H), 2.31 (s, 3H), 2.18 (s, 3H), 1.38 (d, J=6.8 Hz, 3H). $^{13}C\{^1H\}$ NMR: ($CDCl_3$) δ 147.20, 142.36, 135.72, 131.17, 130.30, 128.95, 127.22, 125.09, 116.88, 112.80, 49.64, 22.88, 21.06, 18.37. Anal. Calcd for $C_{16}H_{19}N$: C, 85.29; H, 8.50; N, 6.22. Found: C, 84.98; H, 8.33; N, 5.99.

The scope of catalyst is relatively broad, and results using several reaction conditions are provided in Table 1.

TABLE 1.

Effect of catalyst components and acid on the hydroamination of styrene with aniline.[a]

| Entry | Catalyst | Yield[b] |
|---|---|---|
| 1 | 2% [Pd(PPh$_3$)$_4$] | 0% |
| 2 | 2% Pd(OC(O)CF$_3$)$_2$/8% PPh$_3$ | 28% |
| 3 | 2% [Pd(PPh$_3$)$_4$]/20% TFA | 67% |
| 4 | 2% [Pd(PPh$_3$)$_4$]/20% TfOH | 83% |
| 5 | 2% Pd(OC(O)CF$_3$)$_2$/8% PPh$_3$/20% TFA | 68% |
| 6 | 2% [Pd(OC(O)CF$_3$)$_2$]/3% DPPF | 78% |
| 7 | 2% [Pd(OC(O)CF$_3$)$_2$]/3% DPPF/20% TfOH | >99% |
| 8 | 2% [(DPPF)Pd(OTf)$_2$] | 96% |

[a]Reactions were run for 6 h in toluene solvent at 100° C. Reactions with lower yields did not show complete conversion.
[b]Yields are for isolated material and are an average of two runs.

The scope of this process for different arylamines and different vinylarenes is shown in Table 2.

TABLE 2

Palladium catalyzed hydroamination of vinylarenes.[a]

| | Amine | Olefin | Cond. | time | Yield[b] |
|---|---|---|---|---|---|
| 1 | aniline | styrene | A | 12 h | 83% |
| 2 | aniline | styrene | B | 7 h | >99% |
| 3 | 4-MeO-aniline | styrene | A | 12 h | 93% |
| 4 | 4-MeO-aniline | styrene | B | 7 h | 78% |
| 5 | 4-F$_3$C-aniline | styrene | A | 12 h | 64% |
| 6 | 1-naphthylamine | styrene | B | 7 h | 88% |
| 7 | 2-methylaniline | styrene | B | 7 h | 68% |
| 8 | aniline | 4-F$_3$C-styrene | B | 7 h | 99% |
| 9 | aniline | 2,5-dimethylstyrene | B | 7 h | 85% |
| 10 | aniline | 2-vinylnaphthalene | B | 7 h | 98% |
| 11 | aniline | 2-vinylnaphthalene | C | 72 h | 98% |

TABLE 2-continued

Palladium catalyzed hydroamination of vinylarenes.[a]

| | Amine | Olefin | Cond. | time | Yield[b] |
|---|---|---|---|---|---|
| 12 | PhNHMe | styrene | B | 12 h | 55% |
| 13 | PhNHMe | 2-vinylnaphthalene | A | 12 h | 65% |
| 14 | 4-MeO-C6H4-NHMe | styrene | B[c] | 12 h | 54% |

[a]Reaction conditions: A, 2% Pd(PPh$_3$)$_4$/20% triflic acid, 100° C.; B, 2% Pd(TFA)$_2$/3% DPPF, 20% TfOH, 100° C.; C, 5% (DPPF)Pd(OTf)$_2$, generated from (DPPF)Pd(OTf)$_2$ and AgOTf, 25° C.
[b]Yields are for pure, isolated material and are an average of two runs.
[c]5 mol % catalyst used.

In general, reaction conditions employing 2 mol % catalyst occurred after 6–12 h at 100° C. Some reactions occurred at lower temperatures. The scope of vinylarene encompassed electron-poor to electron neutral styrenes and vinylnaphthalenes. Electron-poor styrenes reacted faster than those that are electron-rich. Styrenes bearing ortho substituents reacted in high yields. Reactions of vinylnaphthalenes were particularly rapid and occurred at room temperature in some cases (Entry 11).

A variety of arylamines gave addition products. 1-Aminonaphthalene reacted in high yield and 2-methyl aniline gave acceptable yields, demonstrating that ortho substituents are tolerated. Electron-rich anisidine and electron-poor trifluoromethylanilines both reacted to form addition products. Reactions of anisidines are particularly valuable because the products can be oxidized with cerric ammonium nitrate or DDQ to provide the parent amine. Reactions of N-alkylanilines also occurred. N-methylaniline and N-methylanisidine added to styrene or naphthalene, although in lower yields than did primary arylamines. Reactions with purely aliphatic amines gave low turnover numbers.

Enantioselective Hydroaminations: A typical procedure is given for the reaction of aniline and 4-(trifluoromethyl)styrene as shown in Scheme 1.

Scheme 1

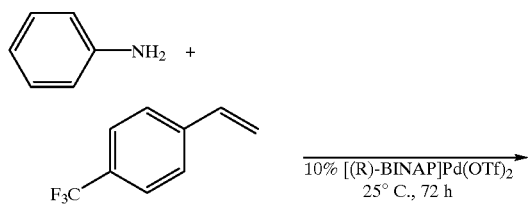

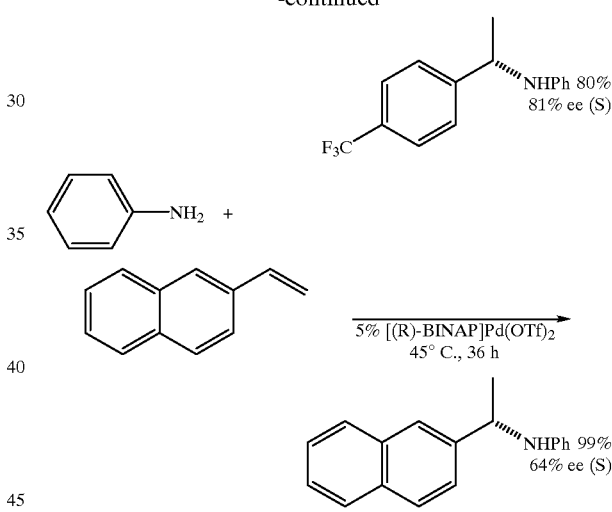

Briefly, [((R)-BINAP)Pd(OTf)$_2$]$^{2+}$(62.0 mg, 0.060 mmol) was suspended in 0.5 mL of toluene in the drybox. The suspension was placed into a vial, which was sealed with a cap containing a PTFE septum, and the vial was removed from the dry box. 4-(Trifluoromethyl)styrene (258 mg, 1.50 mmol) and aniline (93 mg, 1.00 mmol) were added to the reaction mixture by syringe. The reaction mixture was stirred at room temperature for 24 h. The reaction mixture was adsorbed onto silica gel and isolated by eluting with 10% ethyl acetate/hexenes to give 162 mg (62%) of (S)-N-(1-phenylethyl)-N-[4-(trifluoromethyl)phenyl]amine. The enantiomeric purity was determined to be 78% ee (S) by capillary GLC analysis with a chiral stationary phase column (β-Cyclodextrine permethylated). $t_R$=48.7 (S), 49.4 (R) min. Enantiomeric purities of N-Phenyl-N-(1-phenylethyl) amine ($t_R$=8.22 (S), 10.67 (R) min) and N-[1-(2-naphthyl)ethyl]-N-phenylamine ($t_R$=6.99 (S), 9.07 (R) min were determined by HPLC analysis with Daicel CHIRALCEL OD-H (hexenes/i-propanol 98/2).

Preliminary studies indicated that enantiopure bisphosphines provide non-racemic amine product (Scheme 1). We focused on the addition reactions that occurred under the mildest conditions so that we could conduct the enantioselective hydroaminations near room temperature. Reaction of aniline with trifluoromethylstyrene catalyzed by [((R)-BINAP)Pd(OSO$_2$CF$_3$)$_2$] at 25° C. gave the addition product in 81% yield and 81% enantioselectivity. Analysis of the enantioselectivity throughout the reaction showed a constant value at both low and high conversion. These results confirmed the irreversibility of the reaction. Reaction of vinylnaphthalene with styrene at 45° C. with the same catalyst gave quantitative yields and 64% enantiomeric excess (ee).

Examples 15–30

Hydroamination of 1,3-Dienes with Arylamines: Sixteen examples of hydroamination of 1,3-dienes with arylamines are shown in Table 3 below (Entries 1–16). Typical reaction conditions are 0.5 mmol amine, 2 mmol cyclohexadiene, 2 mol % Pd(PPh$_3$)$_4$, 10 mol % TFA, toluene, 25° C., mixed for 24 hours. A typical procedure is given for Entry 1, Table 1: Pd(PPh$_3$)$_4$ (5.8 mg, 0.0050 mmol) was suspended in 0.1 mL of toluene in a screw-capped vial. 1,3-Cyclohexadiene (160 mg, 190 μL, 2.00 mmol) and aniline (46.6 mg, 45.6 μL, 0.500 mmol) were added to the reaction mixture. The vial was sealed with a cap containing a PTFE septum and removed from the drybox. Trifluoroacetic acid (5.7 mg, 3.9 μL, 0.050 mmol) was added to the reaction mixture by syringe. The reaction mixture was then stirred at room temperature for 24 h. All volatile compounds were evaporated under reduced pressure, and the residue was adsorbed onto silica gel. The product was eluted using 0.5% ethyl acetate/hexanes to give 85.5 mg (99%) of N-cyclohex-2-en-1-ylaniline as a colorless oil. Additional compounds were made in a similar fashion and analyzed as follows.

N-cyclohex-2-en-1-ylaniline. Colorless oil, 99% yield. $^1$H NMR (CDCl$_3$) δ 7.22 (m, 2H, CH-arom., meta), 6.73 (tt, 1H, $^3J_{H,H}$=7.3 Hz, $^4J_{H,H}$=1.0 Hz, CH-arom., para), 6.66 (m, 2H, CH-arom., ortho), 5.90 (m, 1H), 5.81 (m, 1H), 4.04 (br s, 1H, CHN), 3.68 (br s, 1H, NH), 2.08 (m, 2H), 1.95 (m, 1H), 1.73 (m, 3H). $^{13}$C{$^1$H} NMR (CDCl$_3$) δ 147.3, 130.3, 129.5, 128.7, 117.3, 113.4, 48.0 (CHN), 29.0, 24.9, 19.8. MS: m/z=173, 145, 93, 77, 51.

N-cyclohex-2-en-1-yl-4-methylaniline. Colorless oil, 85% yield. $^1$H NMR (CDCl$_3$) δ 7.05 (br d, 2H, $^3J_{H,H}$=8.1 Hz), 6.61 (d, 2H, $^3J_{H,H}$=8.4 Hz), 5.90 (m, 1H), 5.82 (m, 1H), 4.26 (br s, 1H, CHN), 3.54 (br s, 1H, NH), 2.31 (s, 3H, CH$_3$) 2.09 (m, 2H), 1.96 (m, 1H), 1.74 (m, 3H). $^{13}$C{$^1$H} NMR (CDCl$_3$) δ 145.0, 130.0, 129.9, 129.0, 126.5, 113.7, 48.4 (CHN), 29.1, 25.4, 19.9 (CH$_3$), 19.4.

N-cyclohex-2-en-1-yl-3-methylaniline. Colorless oil, 89% yield. $^1$H NMR (CDCl$_3$) δ 7.10 (m, 1H), 6.57 (m, 1H), 6.48 (m, 2H), 5.88 (m, 1H), 5.79 (m, 1H), 4.03 (br s, 1H, CHN), 3.62 (br s, 1H, NH), 2.32 (s, 3H, CH$_3$), 2.08 (m, 2H), 1.95 (m, 1H), 1.72 (m, 3H). $^{13}$C{$^1$H} NMR (CDCl$_3$) δ 147.4, 139.2, 130.2, 129.4, 128.9, 118.2, 114.2, 110.5, 48.0 (CHN), 29.1, 25.3, 21.8 (CH$_3$), 19.9. IR (neat): 3402 (NH), 3021 (CH-olef.), 2923, 2859, 2834, 1604, 1588, 1507, 1488. MS: m/z=187, 159, 144, 107. Anal. Calcd. for C$_{13}$H$_{17}$N: C, 83.37; H, 9.15; N, 7.48. Found: C, 83.38; H, 9.04; N, 7.17.

N-cyclohex-2-en-1-yl-2-methylaniline. Colorless oil, 88% yield. $^1$H NMR (CDCl$_3$) δ 7.15 (m, 1H), 7.09 (d, 1H, $^3J_{H,H}$=7.0 Hz), 6.68 (m, 2H), 5.90 (m, 1H), 5.82 (m, 1H), 4.09 (br s, 1H, CHN), 3.52 (br s, 1H, NH), 2.16 (s, 3H, CH$_3$), 2.09 (m, 2H), 1.94 (m, 1H), 1.72 (m, 3H). $^{13}$C{$^1$H} NMR (CDCl$_3$) δ 145.3, 130.5, 130.4, 128.9, 127.3, 122.1, 116.7, 110.3, 47.8 (CHN), 29.0, 25.4, 19.8, 17.8 (CH$_3$). MS: m/z=187, 159, 144, 130, 118, 107. Anal. Calcd. for C$_{13}$H$_{17}$N: C, 83.37; H, 9.15; N, 7.48. Found: C, 83.56; H, 8.88; N, 7.24.

N-cyclohex-2-en-1-yl-4-(trifluoromethyl)aniline. Colorless oil, 91% yield. $^1$H NMR (CDCl$_3$) δ 7.43 (d, 2H, $^3J_{H,H}$=8.5 Hz), 6.63 (d, 2H, $^3J_{H,H}$=8.5 Hz), 5.93 (m, 1H), 5.76 (m, 1H), 4.05 (br s, 2H), 2.10 (m, 2H), 1.95 (m, 1H), 1.74 (m, 3H). $^{13}$C{$^1$H} NMR (CDCl$_3$) δ 149.6, 130.9, 127.6, 126.6 (q, $^3J_{C,F}$=3.7 Hz), 125.0 (q, $^1J_{C,F}$=270.3 Hz), 118.4 (q, $^2J_{C,F}$=32.6 Hz), 112.1, 47.5, 28.6, 25.0, 19.5. $^{19}$F{$^1$H} NMR (CDCl$_3$) δ −63.6 (s). IR (KBr): 3435 (NH), 3028, 2931, 2863, 1617, 1529, 1327. MS: m/z=242, 213, 198, 161, 145, 81. Anal. Calcd. for C$_{13}$H$_{14}$NF$_3$: C, 64.72; H, 5.85; N, 5.81. Found: C, 65.00; H, 5.95; N, 5.61.

Ethyl 4-(cyclohex-2-en-1-ylamino)benzoate. Colorless solid, 96% yield, eluted from silica gel using 20/1 hexanes/ ethyl acetate. $^1$H NMR (CDCl$_3$) δ 7.86 (d, 2H, $^3J_{H,H}$=8.6 Hz), 6.56 (d, 2H, $^3J_{H,H}$=8.6 Hz), 5.89 (m, 1H), 5.73 (m, 1H), 4.32 (q, 2H, $^3J_{H,H}$=7.1 Hz, CH$_2$CH$_3$), 4.15 (br s, 1H, NH), 4.06 (br s, 1H, CHN), 2.05 (m, 2H), 1.92 (m, 1H), 1.69 (m, 3H), 1.36 (t, 3H, $^3J_{H,H}$=7.1 Hz, CH$_2$CH$_3$). $^{13}$C{$^1$H} NMR (CDCl$_3$) δ 167.0 (CO), 151.1, 131.8, 131.0, 127.8, 118.6, 111.9, 60.3 (OCH$_2$CH$_3$), 47.7 (CHN), 28.9, 25.5, 19.7, 14.6 (OCH$_2$CH$_3$). IR (KBr): 3365 (NH), 3024, 2978, 2935, 2863, 1689 (CO), 1605, 1523. MS: m/z=245, 217, 165, 120, 81. Anal. Calcd. for C$_{15}$H$_{19}$NO$_2$: C, 73.44; H, 7.81; N, 5.71. Found: C, 73.26; H, 7.56; N, 5.67.

N-cyclohex-2-en-1-yl-4-methoxyaniline. Colorless oil, 78% yield, eluted from silica gel using 20/1 hexanes/ethyl acetate. $^1$H NMR (CDCl$_3$) δ 6.76 (m, 2H), 6.58 (m, 2H), 5.80 (m, 1H), 5.74 (m, 1H), 3.89 (br s, 1H, CHN), 3.73 (s, 3H, OCH$_3$), 3.26 (br s, 1H, NH), 2.01 (m, 2H), 1.88 (m, 1H), 1.69 (m, 1H), 1.57 (m, 2H). $^{13}$C{$^1$H} NMR (CDCl$_3$) δ 152.1, 141.5, 130.0, 129.0, 115.1, 115.0, 55.9 (OCH$_3$), 49.1 (CHN), 29.1, 25.4, 19.9. MS: m/z=203, 175, 160, 123, 108, 81.

N-cyclohex-2-en-1-yl-3-methoxyaniline. Colorless oil, 95% yield, eluted from silica gel using 20/1 hexanes/ethyl acetate. $^1$H NMR (CDCl$_3$) δ 7.10 (m, 1H), 6.27 (m, 2H), 6.20 (m, 1H), 5.87 (m, 1H), 5.77 (m, 1H), 3.99 (br s, 1H, CHN), 3.79 (S, 3H, OCH$_3$), 3.70 (br s, 1H, NH), 2.05 (m, 2H), 1.92 (m, 1H), 1.69 (m, 3H). $^{13}$C{$^1$H} NMR (CDCl$_3$) δ 161.0, 148.7, 130.4, 130.2, 128.6, 106.6, 102.3, 99.3, 55.2, 48.0, 29.0, 25.3, 19.8. MS: m/z=203, 175, 160, 123, 81. Anal. Calcd. for C$_{13}$H$_{17}$NO: C, 76.81; H. 8.43; N, 6.89. Found: C, 77.19; H, 8.49; N, 6.52.

N-cyclohex-2-en-1-yl-2-methoxyaniline. Colorless oil, 80% yield, eluted from silica gel using 20/1 hexanes/ethyl acetate. $^1$H NMR (CDCl$_3$) δ 6.89 (br t, 1H, $^3J_{H,H}$=7.8 Hz), 6.79 (br d, 1H, $^3J_{H,H}$=7.8 Hz), 6.66 (m, 2H), 5.88 (m, 1H), 5.80 (m, 1H), 4.26 (br s, 1H, NH), 4.02 (br s, 1H, CHN), 3.86 (s, 3H, OCH$_3$), 2.06 (m, 2H), 1.95 (m, 1H), 1.77 (m, 1H), 1.67 (m, 2H). $^{13}$C{$^1$H}NMR (CDCl$_3$) 147.1, 137.2, 130.1, 128.9, 121.4, 116.3, 110.4, 109.7, 55.6, 47.6, 29.0, 25.4, 19.9. MS: m/z=203, 175, 160, 123, 108. Anal. Calcd. for C$_{13}$H$_{17}$NO: C, 76.81; H, 8.43; N, 6.89. Found: C, 77.16; H, 8.56; N, 6.57.

N-cyclohex-2-en-1-yl-2-bromoaniline. Colorless oil, 95% yield. $^1$H NMR (CDCl$_3$) δ 7.44 (dd, 1H, $^3J_{H,H}$=7.9 Hz, $^4J_{H,H}$=1.5 Hz), 7.16 (m, 1H), 6.71 (dd, 1H, $^3J_{H,H}$=8.2 Hz, $^4J_{H,H}$=0.9 Hz), 6.56 (pseudo dt, 1H, $^3J_{H,H}$=7.6 Hz, $^4J_{H,H}$=1.5 Hz), 5.92 (m, 1H), 5.79 (m, 1H), 4.34 (m, 1H), 4.04 (br s, 1H, NH), 2.08 (m, 2H), 1.92 (m, 1H), 1.71 (m, 3H). $^{13}$C{$^1$H} NMR (CDCl$_3$) δ 144.2, 132.8, 130.9, 128.6, 128.1, 117.6, 111.9, 110.1, 48.0 (CHN), 28.8, 25.3, 19.7. MS: m/z=251, 233, 171, 144, 81.

N-cyclohex-2-en-1-ylnaphthalene-2-amine. Colorless oil, 96% yield. $^1$H NMR (CDCl$_3$) δ 7.68 (m, 3H), 7.41 (m, 1H), 7.24 (m, 1H), 6.92 (m, 1H), 6.90 (s, 1H), 5.94 (m, 1H), 5.87 (m, 1H), 4.18 (br s, 1H, CHN), 3.86 (br s, 1H, NH), 2.11 (m, 2H), 2.02 (m, 1H), 1.75 (m, 3H). $^{13}$C{$^1$H} NMR (CDCl$_3$) δ 144.9, 135.4, 130.5, 129.2, 128.5, 127.8, 127.7, 126.5, 126.0, 122.0, 118.5, 105.1, 48.1 (CHN), 28.9, 25.4, 19.9. IR (neat): 3406 (NH), 3048, 3021, 2930, 2859, 2833, 1628, 1602, 1519, 1481. MS: m/z=223, 195, 143, 115. Anal. Calcd. for C$_{16}$H$_{17}$N: C, 86.05; H, 7.67; N, 6.27. Found: C, 85.83; H, 7.44; N, 5.99.

N-cyclohex-2-en-1-ylnaphthalene-1-amine. Colorless oil, 97% yield. $^1$H NMR (CDCl$_3$) δ 7.88 (m, 2H), 7.50 (m, 3H), 7.32 (d, 1H, $^3J_{H,H}$=8.0 Hz), 6.77 (d, 1H, $^3J_{H,H}$=7.5 Hz), 5.99 (m, 2H), 4.47 (br s, 1H, NH), 4.29 (br s, 1H, CHN), 2.13 (m, 3H), 1.81 (m, 3H). $^{13}$C{$^1$H} NMR (CDCl$_3$) δ 142.3, 134.7, 130.7, 128.9, 128.5, 126.8, 125.8, 124.7, 123.6, 120.0, 117.1, 104.8, 48.0 (CHN), 28.7, 25.4, 19.9. IR (neat): 3431 (NH), 3057, 3021, 2924, 2859, 2833, 1580, 1524, 1476, 1407. MS: m/z=223, 143, 115. Anal. Calcd. for C$_{16}$H$_{17}$N: C, 86.05; H, 7.67; N, 6.27. Found: C, 85.85; H, 7.78; N, 6.18.

2-(N-cyclohex-2-en-1-yl)pyridine. Cream colored solid, 79% yield. $^1$H NMR (CDCl$_3$) δ 8.08 (m, 1H), 7.39 (m, 1H), 6.54 (m, 1H), 6.41 (d, 1H, $^3J_{H,H}$=8.4 Hz), 5.87 (m, 1H), 5.74 (m, 1H), 4.51 (br d, 1H, $^3J_{H,H}$=6.9 Hz, NH), 4.32 (br m, 1H, CHN), 2.00 (m, 3H), 1.69 (m, 3H). $^{13}$C{$^1$H} NMR (CDCl$_3$) δ 158.2, 148.5, 137.5, 130.5, 128.6, 112.8, 107.3, 46.6 (CHN), 29.4, 25.2, 19.9. IR (KBr): 3260 (NH), 3021, 2921, 1612, 1520, 1486. MS: m/z=174, 145, 119, 94, 79. Anal. Calcd. for C$_{11}$H$_{14}$N$_2$: C, 75.82; H, 8.10; N, 16.08. Found: C, 75.56; H, 8.18; N, 15.81.

3-(N-cyclohex-2-en-1-yl)pyridine. Cream colored solid, 88% yield. $^1$H NMR (CDCl$_3$) δ 8.03 (d, 1H, $^4J_{H,H}$=2.8 Hz), 7.94 (dd, 1H, $^3J_{H,H}$=4.6 Hz, $^4J_{H,H}$=1.1 Hz), 7.07 (dd, 1H, $^3J_{H,H}$=8.1 Hz, $^3J_{H,H}$=4.6 Hz), 6.89 (ddd, 1H, $^3J_{H,H}$=8.3 Hz, $^4J_{H,H}$=2.8 Hz, $^4J_{H,H}$=1.2 Hz), 5.89 (m, 1H), 5.73 (m, 1H), 3.98 (br s, 1H), 3.70 (br s, 1H), 2.06 (m, 2H), 1.91 (m, 2H), 1.69 (m, 3H). $^{13}$C{$^1$H}NMR (CDCl$_3$) δ 143.4, 138.7, 136.7, 131.0, 128.0, 123.9, 119.1, 47.9 (CHN), 28.9, 25.3, 19.7. IR (KBr): 3256 (NH), 3024, 2929, 2859, 2833, 1586, 1481. MS: m/z=174, 145, 94, 81. Anal. Calcd. for C$_{11}$H$_{14}$N$_2$: C, 75.82; H, 8.10; N, 16.08. Found: C, 75.62; H, 7.98; N, 15.88.

N-cyclohex-2-en-1-yl-N-methylaniline. Colorless oil, 97% yield. $^1$H NMR (CDCl$_3$) δ 7.43 (m, 2H, CH-arom., meta), 6.99 (br d, 2H, $^3J_{H,H}$=8.1 Hz, CH-arom., ortho), 6.89 (br t, 1H, $^3J_{H,H}$=7.3 Hz, CH-arom., para), 6.11 (m, 1H), 5.83 (m, 1H), 4.66 (m, 1H, CHN), 2.98 (s, 3H, NCH$_3$), 2.25 (m, 2H), 2.04 (m, 2H), 1.82 (m, 2H). $^{13}$C{$^1$H} NMR (CDCl$_3$) δ 149.9, 130.8, 130.1, 129.3, 116.4, 113.0, 55.1 (CHN), 32.6 (CH$_3$), 25.5, 25.1, 21.7. MS: m/z=187, 159, 144, 107, 77, 51.

N-cyclohex-2-en-1-yl-4-methoxy-N-methylaniline. Colorless oil, 98% yield. $^1$H NMR (CDCl$_3$) δ 6.85 (m, 4H), 5.92 (m, 1H), 5.69 (m, 1H), 4.34 (br m, 1H, CHN), 3.79 (S, 3H, OCH$_3$), 2.77 (s, 3H, NCH$_3$), 2.06 (m, 2H), 1.84 (m, 2H), 1.63 (m, 2H). $^{13}$C{$^1$H} NMR (CDCl$_3$) δ 151.9, 144.8, 130.5, 130.3, 115.6, 114.8, 56.7 (CHN), 55.9 (OCH$_3$), 33.2 (NCH$_3$), 25.2, 25.0, 21.8. IR (neat): 3020, 2989, 2933, 2860, 2832, 1515. MS: m/z=217, 189, 174, 136, 122. Anal. Calcd. for C$_{14}$H$_{19}$N: C, 77.38; H, 8.81; N, 6.45. Found: C, 77.32; H, 8.86; N, 6.39.

N-cyclohept-2-en-1-ylaniline. Colorless oil, 71% yield. $^1$H NMR (CDCl$_3$) δ 7.22 (m, 2H), 6.73 (tt, 1H, $^3J_{H,H}$=7.3 Hz, $^4J_{H,H}$=1.0 Hz, CH-arom., para), 6.62 (m, 2H), 5.88 (m, 1H), 5.73 (m, 1H), 4.13 (br d, 1H, $^3J_{H,H}$=9.5 Hz), 3.76 (br s, 1H), 2.24 (m, 2H), 2.00 (m, 2H), 1.76 (m, 2H), 1.41 (m, 1H). $^{13}$C{$^1$H} NMR (CDCl$_3$) δ 147.3, 137.5, 131.6, 129.4, 117.3, 113.6, 54.1 (CHN), 34.0, 28.9, 28.8, 26.8. IR (neat): 3406 (NH), 3050, 3020, 2922, 2852, 1603, 1503, 1444, 1435, 1320. MS: m/z=187, 158, 93, 77. Anal. Calcd. for C$_{13}$H$_{17}$N: C, 83.37; H, 9.15; N, 7.48. Found: C, 83.29; H, 9.09; N, 7.49.

N-(2,3-dimethylbut-2-enyl)aniline. Colorless oil, 89% yield. $^1$H NMR (CDCl$_3$) δ 7.20 (m, 2H, CH-arom., meta), 6.73 (br t, 1H, $^3J_{H,H}$=7.2 Hz, CH-arom., para), 6.62 (br d, 2H, $^3J_{H,H}$=8.5 Hz, CH-arom., ortho), 3.69 (m, 2H, CH$_2$N), 3.57 (br s, 1H, NH), 1.78 (s, 6H, 2 CH$_3$), 1.73 (s, 3H, CH$_3$). $^{13}$C{$^1$H} NMR (CDCl$_3$) δ 149.0, 129.4, 129.0, 125.4, 117.2, 112.8, 47.3 (CH$_2$N), 21.0, 20.4, 17.7. IR (neat): 3416, 3050, 3017, 2989, 2914, 2859, 1603, 1505, 1484, 1426, 1317. MS: m/z=175, 93, 77, 55. Anal. Calcd. for C$_{12}$H$_{17}$N: C, 82.23; H, 9.78; N, 7.99. Found: C, 82.16; H, 9.81; N, 7.83.

N,N-bis(2,3-dimethyl-2-enyl)aniline. Colorless crystals, 6% yield, eluted from silica before the monoallyl product. $^1$H NMR (CDCl$_3$) δ 7.19 (m, 2H), 6.69 (m, 3H), 3.90 (s, 4H, 2 CH$_2$N), 1.77 (s, 6H, 2 CH$_3$), 1.71 (s, 6H, 2 CH$_3$), 1.56 (s, 6H, 2 CH$_3$) $^{13}$C{$^1$H} NMR (CDCl$_3$) δ 150.3, 129.1, 126.9, 126.4, 115.9, 112.9, 52.4 (CH$_2$N), 21.3, 20.1, 15.8. IR (KBr): 3024, 2989, 2915, 2856, 1508, 1373, 1346. MS: m/z=257, 175, 160, 93, 77, 55. Anal. Calcd. for C$_{18}$H$_{27}$N: C, 84.00; H, 10.57; N, 5.44. Found: C, 84.00; H, 10.67; N, 5.24.

N-(2,3-dimethylbut-2-enyl)-N-methylaniline. Colorless oil, 84% yield. $^1$H NMR (CDCl$_3$) δ 7.32 (m, 2H, CH-arom., meta), 6.83 (br d, 2H, $^3J_{H,H}$=8.6 Hz, CH-arom., ortho), 6.77 (t, 1H, $^3J_{H,H}$=7.3 Hz, CH-arom., para), 3.98 (s, 2H), 2.91 (s, 3H, NCH$_3$), 1.87 (s, 3H, CH$_3$), 1.83 (s, 3H, CH$_3$), 1.70 (s, 3H, CH$_3$). $^{13}$C{$^1$H} NMR δ 150.8, 129.2, 127.6, 126.0, 116.3, 112.7, 54.7 (CH$_2$N), 37.1 (NCH$_3$), 21.2, 20.2, 16.1. IR (neat): 3092, 3061, 3024, 2988, 2916, 2861, 2811. MS: m/z=189, 120, 107, 77, 55. Anal. Calcd. for C$_{13}$H$_{19}$N: C, 82.48; H. 10.12; N, 7.40. Found: C, 82.60; H, 10.20; N, 7.40.

N-(3-methylbut-2-enyl)aniline. Colorless oil, 73% yield. $^1$H NMR (CDCl$_3$) δ 7.20 (m, 2H), 6.72 (tt, 1H, $^3J_{H,H}$=7.3 Hz, $^4J_{H,H}$=1,0 Hz, CH-arom., para), 6.63 (m, 2H), 5.35 (m, 1H, H-olef.), 3.71 (m, 2H, CH$_2$N), 3.65 (br s, 1H, NH), 1.77 (s, 3H, CH$_3$), 1.73 (s, 3H, CH$_3$). $^{13}$C{1H}(CDCl$_3$) NMR δ 148.6, 135.8, 129.4, 121.8, 117.5, 113.0, 42.2 (CH$_2$N), 25.9,18.2. MS: m/z=161, 146, 93, 77.

N-(3-methylbut-2-enyl)-N-methylaniline. Colorless oil, 84% yield. $^1$H NMR (CDCl$_3$) δ 7.24 (pseudo t, 2H, $^3J_{H,H}$=7.3 Hz, CH-arom., meta), 6.75 (d, 2H, $^3J_{H,H}$=7.3 Hz, CH-arom., ortho), 6.72 (t, 1H, $^3J_{H,H}$=7.3 Hz, CH-arom., para), 5.22 (t, 1H, $^3J_{H,H}$=6.5 Hz, H-olef.), 3.90 (d, 2H, $^3J_{H,H}$=6.5 Hz, CH$_2$N), 2.91 (s, 3H, NCH$_3$), 1.73 (s, 3H, CH$_3$), 1.72 (s, 3H, CH$_3$). $^{13}$C{$^1$H} NMR (CDCl$_3$) 150.0, 134.6, 129.2, 121.1, 116.6, 113.1, 50.6 (CH$_2$N), 38.0 (NCH$_3$), 25.8, 18.9. MS: m/z=175, 160, 107, 77.

Table 3 shows results from preparative reactions evaluating substrate scope using 2 mol % Pd(PPh$_3$)$_4$ and 10 mol % TFA.

TABLE 3

Pd-catalyzed addition of arylamines to cyclonexadiene.

| Entry | Amine | Yield[b] (%) |
|---|---|---|
| 1 | ⟨benzene⟩-NH$_2$ | 99 |
| 2 | Me-⟨benzene⟩-NH$_2$ | 85 |

TABLE 3-continued

Pd-catalyzed addition of arylamines to cyclonexadiene.

| Entry | Amine | Yield[b] (%) |
|---|---|---|
| 3 | 3-methylaniline | 89 |
| 4 | 2-methylaniline | 88 |
| 5[c] | 4-(trifluoromethyl)aniline | 91 |
| 6[c] | ethyl 4-aminobenzoate | 96 |
| 7 | 4-methoxyaniline | 78 |
| 8 | 3-methoxyaniline | 95 |
| 9 | 2-methoxyaniline | 80 |
| 10 | 2-bromoaniline | 95 |
| 11 | 2-aminonaphthalene | 96 |
| 12 | 1-aminonaphthalene | 97 |
| 13[d] | 2-aminopyridine | 79 |
| 14[d] | 3-aminopyridine | 88 |
| 15 | N-methylaniline | 97 |
| 16 | 4-methoxy-N-methylaniline | 98 |

[a]Reaction conditions: 0.5 mmol amine, 2 mmol cyclohexadiene, 2 mol % Pd(PPh$_3$)$_4$, 10 mol % TFA, toluene, 25° C., 24 h.
[b]Yields are for pure, isolated compounds and are an average of two runs.
[c]Reaction time: 48 h.
[d]Reaction conditions: 2.5 mol % [Pd($\pi$-allyl)Cl]$_2$, 10 mol % PPh$_3$, toluene, 100° C., 24 h.

The reactions shown in Table 3 were typically run at room temperature in toluene for 24 h, but shorter times could be used. All reactions occurred in high yield regardless of the presence of an electron-withdrawing, electron-donating, or ortho-substituent on the aniline. Both the electron-rich (entries 7, 9) and electron-poor anilines (entries 5, 6) gave the addition products in high yields, although reactions of the electron-poor anilines required longer times. Reaction of o-toluidine, o-anisidine, o-bromoaniline and 1-aminonaphthalene showed that ortho-substituents are tolerated. Addition of N-alkylanilines also occurred under standard conditions (entries 15, 16). However, pyridylamines reacted only in the absence of acid cocatalyst. Reactions at 100° C. using [Pd($\pi$-allyl)Cl]$_2$/PPh$_3$ as catalyst gave high yields of the pyridylamine products (entries 13, 14). Anisyl groups can be removed by oxidation; thus, reactions of anisidine and N-alkyl anisidine are the synthetic equivalent of adding primary alkylamines or ammonia.

The scope of the process for different 1,3-dienes is provided in Table 4.

TABLE 4

Reactions of Aniline with various Dienes

| Entry | Diene | Amine | Yield[a] (%) |
|---|---|---|---|
| 1[b] | cycloheptadiene | PhNH$_2$ | 71 |
| 2[c] | 2,3-dimethylbutadiene | PhNH$_2$ | 89[d] |

TABLE 4-continued

Reactions of Aniline with various Dienes

| Entry | Diene | Amine | Yield[a] (%) |
|---|---|---|---|
| 3[c] | 2-methyl-1,3-butadiene (isoprene) | PhNHMe | 84 |
| 4[e] | 2-methyl-1,3-butadiene (isoprene) | PhNH$_2$ | 73 |
| 5[b] | 1,3-butadiene | PhNHMe | 84 |

[a]Yields are for pure, isolated compounds and are an average of two runs.
[b]Reaction conditions: 0.5 mmol amine, 2 mmol diene, 1 mol % Pd(PPh$_3$)$_4$, 50 mol % acetic acid.
[c]Same reaction conditions except 2 mol % Pd(PPh$_3$)$_4$, 10 mol % TFA.
[d]6% of diallyl amine obtained for this reaction with excess diene.
[e]Four-fold excess of aniline used.

As shown in Table 4, cycloheptadiene reacted slower than cyclohexadiene, but gave good yields. Reactions of acyclic dienes occurred in good yields in many cases, but the scope was less straightforward than that for cyclic dienes. The reaction of aniline with 2,3-dimethyl-1,3-butadiene formed the 1:1-adduct as the major product, and formation of the competing N,N-diallyl amine product was suppressed by using a four-fold excess of aniline. Isoprene reacted with aniline and N-methylaniline to give almost exclusively a single product from reaction at the less hindered end of the diene, whereas butadiene gave complex reaction mixtures.

Example 31

Nickel Catalyzed Addition of morpholine to 1,3-Cyclohexadiene to form 4-(2-Cyclohexenyl)morpholine Ni(cod)$_2$ (11.0 mg, 0.040 mmol) and DPPF (44.0 mg, 0.080 mmol) were suspended in 0.3 mL of toluene in a screw-capped vial. The vial was sealed with a cap containing a PTFE septum and removed from the dry box. 1,3-Cyclohexadiene (160 mg, 2.00 mmol), morpholine (183 mg, 2.10 mmol) and trifluoroacetic acid (9.0 mg, 0.080 mmol) were added to the reaction mixture by syringe. The reaction mixture was stirred at room temperature for 14 h. The volatile compounds were evaporated under reduced pressure, and the residue was adsorbed onto silica gel. The product was eluted with 90% ethyl acetate/hexanes to give 274 mg (82%) of 4-(2-cyclohexenyl)morpholine: $^1$H NMR (500 MHz, [D]chloroform, 25° C.): δ=5.84–5.83 (m, 1H; H-C3), 5.68–5.66 (m, 1H; H-C2), 3.74–3.72 (m, 4H; CH$_2$), 3.17 (brs, 1H; H-C1), 2.64–2.56 (m, 4H; CH$_2$), 2.00–1.98 (m, 2H; CH$_2$), 1.82–1.80 (m, 2H; CH$_2$), 1.57–1.54 (m, 2H; CH$_2$); $^{13}$C{$^1$H} NMR (125 MHz, [D]chloroform, 25° C.): δ=130.08, 128.77, 67.34, 60.22, 49.12, 25.15, 23.07, 21.29.

Examples 32–43

Enantioselective Hydroamination Reactions:

Twelve enantioselective Examples are shown in Table 5 below (entries 1–12). A typical procedure is as follows: [Pd(π-allyl)Cl]$_2$ (2.3 mg, 0.0063 mmol) and the (R,R)-Naphthyl-Trost ligand (10.9 mg, 0.0138 mmol) were dissolved in 0.1 mL of dry THF in a screw-capped vial. After stirring for one min, aniline (11.4 μL, 0.125 mmol) was added, and the color of the solution turned bright yellow. After addition of cyclohexadiene (47.6 μL, 0.500 mmol), the vial was sealed with a cap that contained a PTFE septum, and the reaction mixture was stirred at room temperature for 120 h. After removal of all volatile compounds using a rotary evaporator, the residue was purified by chromatography on silica gel (Hexanes : EtOAc=200:1) to give 18.8 mg (87%) of N-cyclohex-2-en-1-ylaniline as a colorless oil with 89% ee and the $[\alpha]_D^{24°\,C.}$ value of −84.5 (c 1.0222, CH$_2$Cl$_2$)

Determination of Enantiomeric Excess and Absolute Configuration.

The values for enantiomeric excess were determined by chiral stationary phase HPLC using a Daicel Chiralcel OJ column (flow 0.5 mL/min with hexanes as eluent). The two enantiomers showed retention times of 41.2 min and 44.3 min. To assign the absolute configuration of the enantiomers, the product was synthesized independently by the arylation of commercially available (S)-2-cyclohexen-l-amine (95% ee) with phenyl bromide applying a previously reported method (For chiral amines, see: Wagaw, S.; Rennels, R. A.; Buchwald, S. L. *J. Am. Chem. Soc.* 1997, 119, 8451–8458. For allylic amines, see: Wolfe, J. P.; Buchwald, S. L. *J. Org. Chem.* 2000, 65, 1144–1157). The product of the arylation was obtained in 95% ee and a retention time of 43.8 min by the above HPLC conditions. These results showed that the more rapidly eluting enantiomer has the (R)-configuration, the more slowly eluting enantiomer the (S)-configuration. Alternatively, the enantiomeric excess of the products were determined by using a Daicel Chiralcel OD-H column with the following mixtures of solvents and flow rates: Table 5, Entry 7: 20.5 and 23.3 min (flow 1.0 mL/min, pure hexanes); Table 5, Entry 9: 21.4 and 24.6 min (flow 1.0 mL/min, pure hexanes); Table 5, Entry 10: 22.4 and 24.6 min (flow 1.0 mL/min, pure hexanes); Table 3, Entry 11: 15.5 and 16.4 min (flow 0.5 mL/min, hexanes : $^i$PrOH=20:1); Table 5, Entry 12: 20.8 and 21.6 min (flow 0.5 mL/min, pure hexanes). As with the OJ column, the enantiomer with the (R)-configuration eluted more rapidly than that with the (S)-configuration. The absolute configurations for the other addition products were assigned in analogy to those determined for the aniline addition product. The two enantiomers from the reaction of aniline with cycloheptadiene were detected at 23.8 and 26.8 min (OD-H, flow 1.0 mL/min, pure hexanes as eluent).

The results of the enantioselective hydroaminations are shown in Table 5.

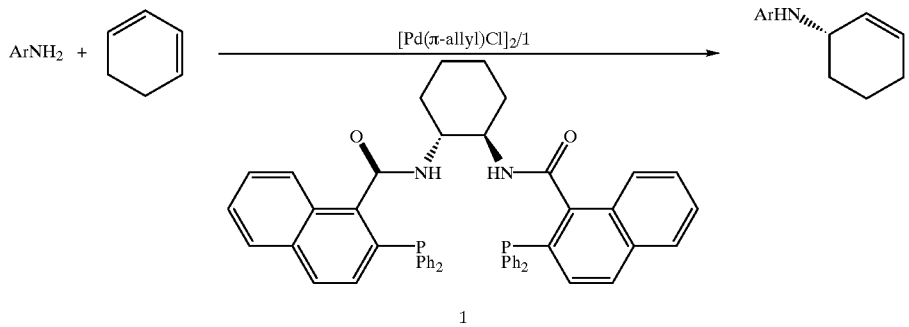

1

TABLE 5

Enantioselective addition of arylamines to cyclohexadiene

| Entry | Amine | Ligand | M | Time | Yield[a] (%) | ee[b] (%) |
|---|---|---|---|---|---|---|
| 1[c] | PhNH$_2$ | (R,R)-1 | 1.2 | 72 h | 61 | 91 (S) |
| 2[c] | PhNH$_2$ | (R,R)-Trost | 1.2 | 72 h | 65 | 11 (S) |
| 3[c] | PhNH$_2$ | (R)-BINAP | 1.2 | 72 h | 99 | 7 (R) |
| 4[c] | PhNH$_2$ | (S,S)-DIOP | 1.2 | 72 h | 84 | 4 (R) |
| 5[c] | PhNH$_2$ | (S,S)-BDPP[e] | 1.2 | 72 h | 31 | 34 (R) |
| 6[c] | PhNH$_2$ | (R,R)-1 | Neat | 72 h | 94 | 50 (S) |
| 7[d] | PhNH$_2$ | (R,R)-1 | 1.2 | 120 h | 87 | 89 (S) |
| 8[d] | PhNH$_2$ | (R,R)-1 | 0.6 | 120 h | 63 | 92 (S) |
| 9[d] | p-MeC$_6$H$_4$NH$_2$ | (R,R)-1 | 1.2 | 120 h | 78 | 86 (S) |
| 10[d] | o-MeC$_6$H$_4$NH$_2$ | (R,R)-1 | 1.2 | 120 h | 59 | 90 (S) |
| 11[d] | p-EtO$_2$CC$_6$H$_4$NH$_2$ | (R,R)-1 | 1.2 | 120 h | 83 | 95 (S) |
| 12[d] | p-F$_3$CC$_6$H$_4$NH$_2$ | (R,R)-1 | 1.2 | 120 h | 73 | 95 (S) |

[a]Yields are for pure, isolated compounds.
[b]Values for ee were determined by chiral HPLC; assignment of absolute configuration by comparison with retention time of product synthesized by arylation of commercially available (S)-2-cyclohexen-1-amine with phenyl bromide applying a previously reported method (arylation of chiral amines: Waqaw, S.; Rennels, R. A.; Buchwald, S. L. J. Am. Chem. Soc. 1997, 119, 8451–8458; of allylic amines: Wolfe, J. P.; Buchwald, S. L. J. Org. Chem. 2000, 65, 1144–1157).
[c]Reaction conditions: 0.25 mmol aniline, 1 mmol cyclohexadiene, 2.5 mol % [Pd($\pi$-allyl)Cl]$_2$, 5 mol % ligand.
[d]Reaction conditions: 0.125 mmol aniline, 0.5 mmol cyclohexadiene, 5 mol % [Pd($\pi$-allyl)Cl]$_2$, 11 mol % ligand.
[e](2S,4S)-(−)-2,4-Bis(diphenylphosphino)pentane.

Experiments with added TFA using various optically active phosphines instead of PPh$_3$ and [Pd($\pi$-allyl)Cl]$_2$ as catalyst precursors showed good conversions but little or no stereoselection. Although slower, the reaction without added acid using a catalyst comprised of [Pd($\pi$-allyl)Cl]$_2$ and Trost's ligand 1, a naphthyl version of the parent ligand in entry 2 in Table 5, showed a promising combination of stereoselection and conversion. Optimization of reaction conditions showed that 5 molt % [Pd($\pi$-allyl)Cl]$_2$ and 11 mol % ligand 1 at 1.25 mM in THF solvent at room temperature provided the highest combination of yield and enantioselectivity for a broad range of arylamines (entries 7, 9–12). Higher temperatures provided lower final conversions, presumably because of catalyst deactivation. Monitoring of the reaction by HPLC showed that the enantioselectivity was constant throughout the reaction, demonstrating that the process is favorable enough thermodynamically, even without telomerization, to be irreversible. Applying the same conditions to the reaction of cycloheptadiene gave the 1,4 addition product in 22% yield with 66% ee.

Examples 44–67

Palladium Catalyzed Addition of Piperidine to Activated Olefins and Palladium Catalyzed Addition of Primary Amines to Activated Olefins Twenty-four examples of palladium catalyzed addition of piperidine to activated olefins and palladium catalyzed addition of primary amines to activated olefins are shown it Table 6 (entries 1–24).

The reaction conditions and results for the palladium catalyzed addition of piperidine to activated olefins are shown in Table 6 (entries 1–7 and 10–20). A typical procedure is given for the reaction in entry 2. The reaction conditions and results for the palladium catalyzed addition of primary amines to activated olefins are shown in Table 6 (entries 8,9 and 21–24). A typical procedure is given for the reaction in entry 23. The procedures for the production of each of the products is as follows.

1-Methyl-2-piperidinoethyl cyanide: Pd(OAc)$_2$ (4.5 mg, 0.020 mmol), 1,3-Bis[(di-tert-butylphosphino)methyl] benzene (7.9 mg, 0.002 mmol) and 1,3,5-trimethoxybenzene (168 mg, 1.00 mmol; internal standard) were suspended in 0.5 mL of toluene in a screw-capped vial. The vial was sealed with a cap that contained a PTFE septum and was removed from the dry box. Methacrylonitrile (270 mg, 4.00 mmol) and piperidine (85.0 mg, 1.00 mmol) were added to the reaction mixture by syringe. The reaction mixture was stirred at room temperature for 12 h. The yield of 1-methyl-2-piperidinoethyl cyanide was determined by GLC analysis (99%). The product was isolated by silica gel column chromatography (50% ethyl acetate/hexanes) to give 310 mg (100%) of 1-methyl-2-piperidinoethyl cyanide. $^1$H NMR: (C$_6$D$_6$) δ 2.80–2.75 (m, 1H), 2.59 (dd, J=12.6 Hz, 8.1 Hz, 1H), 2.44–2.41 (m, 4H), 2.38 (dd, J=12.6, 6.5 Hz, 1H), 1.60–1.56 (m, 4H), 1.45–1.41 (m, 2H), 1.30 (d, J=7.1 Hz, 3H). $^{13}$C{$^1$H} NMR: (C$_6$D$_6$) δ 122.71, 61.74, 54.62, 25.86, 24.21, 24.10, 16.05.

2-Piperidinopropyl cyanide: 97% yield, eluted from silica gel using 50/50 hexanes/ethyl acetate. $^1$H NMR: (CDCl$_3$) δ 3.04–2.98 (m, 1H), 2.53 (dd, J=16.6, 5.4 Hz, 1H), 2.52–2.48 (m, 2H), 2.46–2.45 (m, 2H; CH$_2$), 2.34 (dd, J=16.6, 7.8 Hz, 1H), 1.61–1.56 (m, 4H), 1.46–1.41 (m, 2H), 1.21 (d, J=6.7 Hz, 3H). $^{13}$C{$^1$H} NMR: (CDCl$_3$) δ 118.98, 56.70, 49.34, 26.17, 24.56, 20.52, 15.28.

Ethyl 3-piperidinobutanoate: 90% yield, eluted from silica gel using 30/70 hexanes/ethyl acetate. $^1$H NMR: (CDCl$_3$) δ 4.13 (q, J=7.0 Hz, 2H), 3.12 (m, 1H), 2.58 (dd, J=14.2, 5.5 Hz, 1H), 2.45–2.43 (m, 4H), 2.21 (dd, J=14.2, 8.5 Hz, 1H), 1.56–1.53 (m, 4H), 1.44–1.41 (m, 2H), 1.26 (t, J=7.0 Hz, 3H), 1.05 (d, J=6.7 Hz, 3H). $^{13}$C{$^1$H} NMR: (CDCl$_3$) δ 172.64, 59.96, 57.00, 49.32, 38.19, 26.37, 24.79, 14.18, 14.17.

Ethyl 2-methyl-3-piperidinopropanoate: 99% yield, eluted from silica gel using 30/70 hexanes/ethyl acetate. $^1$H NMR: (CDCl$_3$) δ 4.14 (q, J=7.3 Hz, 2H), 2.71–2.65 (m, 1H), 2.61 (dd, J=12.1, 8.7 Hz, 1H), 2.42–2.35 (m, 2H), 2.35–2.30 (m, 2H), 2.27 (dd, J=12.1, 6.0 Hz, 1H), 1.51–1.56 (m, 4H), 1.41–1.37 (m, 2H), 1.26 (t, J=7.3 Hz, 3H), 1.13 (d, J=6.8 Hz, 3H). $^{13}$C{$^1$H} NMR: (CDCl$_3$) δ 76.05, 62.34, 59.86, 54.56, 37.91, 25.96, 24.30, 15.48, 14.14.

2-Anilino-1-methylethyl cyanide: Pd(TFA)$_2$ (33.0 mg, 0.10 mmol) and 2,6-Bis[(di-tert-butylphosphino)methyl]pyridine (40.0 mg, 0.10 mmol) were suspended in 0.5 mL of toluene in a screw-capped vial. The vial was sealed with a cap containing a PTFE septum and removed from the dry box. Methacrylonitrile (270 mg, 4.00 mmol) and aniline (93.1 mg, 1.00 mmol) were added to the reaction mixture by syringe. The reaction mixture was stirred at room temperature for 24 h, after which time it was adsorbed onto silica gel. The product was isolated by eluting with 15% ethyl acetate/hexanes to give 142 mg (89%) of 2-anilino-1-methylethyl cyanide. $^1$H NMR: (CDCl$_3$) δ 7.22 (t, J=7.6 Hz, 2H), 6.78 (t, J=7.6 Hz, 1H), 6.63 (d, J=7.6 Hz, 2H), 3.71 (brs, 1H) 3.43 (dd, J=13.8, 8.0 Hz, 1H), 3.37 (dd, J=13.8, 6.0 Hz, 1H), 2.99 (m, 1H), 1.38 (d, J=7.1 Hz, 3H). $^{13}$C{$^1$H} NMR: (CDCl$_3$) δ 146.52, 129.50, 121.81, 118.50, 113.04, 47.04, 25.98, 15.39. Anal. Calcd. for C$_{10}$H$_{12}$N$_2$: C, 74.97; H, 7.55; N, 17.48. Found: C, 74.75; H, 7.35; N, 17.57.

2-Anilinopropyl cyanide: 90% yield, eluted from silica gel using 80/20 hexanes/ethyl acetate. $^1$H NMR: (CDCl$_3$) δ 7.22 (t, J=7.5 Hz, 2H), 6.79 (t, J=7.5 Hz, 1H), 6.61 (d, J=7.5 Hz, 2H), 3.90 (m, 1H), 3.70 (brs, 1H), 2.63 (brd, J=2.3 Hz, 1H), 2.61 (brs, 1H), 1.45 (d, J=6.5 Hz, 3H). $^{13}$C{$^1$H} NMR: (CDCl$_3$) δ 145.76, 129.62, 118.53, 117.60, 113.60, 45.45, 24.33, 20.40.

2-(Butylamino)-1-methylethyl cyanide: 81% yield, eluted from silica gel using 90/10 hexanes/ethyl acetate. $^1$H NMR: (CDCl$_3$) δ 2.88–2.74 (m, 4H), 2.64 (m, 1H), 1.51–1.42 (m, 2H), 1.42 (brs, 1H), 1.39–1.32 (m, 2H), 1.32 (d, J=6.7 Hz, 3H), 0.92 (t, J=7.4 Hz, 3H). $^{13}$C{1H} NMR: (CDCl$_3$) δ 122.28, 52.49, 49.09, 32.09, 26.57, 20.22, 15.58, 13.84.

Table 6 summarizes the synthetic results for addition of amines to acrylic acid derivatives using transition metal catalysts.

TABLE 6

Transition metal-catalyzed addition of amines to activated olefins.[a]

| Entry | Amine | Olefin | Catalyst, mol% | Conditions | Yield[b] |
|---|---|---|---|---|---|
| 1 | piperidine | CH$_2$=C(CH$_3$)CN | Pd(OAc)$_2$, 2% | RT, 12 h | 12% |
| 2 | | | Pd(OAc)$_2$, 2%/ PCP 1, 2% | RT, 12 h | 98% |
| 3 | | | Pd(TFA)$_2$, 2% | RT, 12 h | 96% |
| 4 | | | Pd(TFA)$_2$, 2%/ PNP 2, 2% | RT, 12 h | 99% |
| 5 | | | | | 99% |
| 6 | | | [Rh(cod)$_2$]BF$_4$, 2% | RT, 8 h | 90% |
| 7 | | | [Ir(cod)$_2$]BF$_4$, 2% | RT, 8 h | 96% |
| | | | [RuCl$_2$(p-Cymene)]$_2$, 2.5% | RT, 12 h | |
| 8 | n-BuNH$_2$ | CH$_2$=C(CH$_3$)CN | Pd(OAc)$_2$, 10% | RT, 18 h | 0% |
| 9 | | | Pd(OAc)$_2$, 2%/ PCP 1, 2% | RT, 12 h | 76% |
| 10 | piperidine | CH$_3$CH=CHCN | Pd(TFA)$_2$, 2% | RT, 12 h | 21% |
| 11 | | | Pd(TFA)$_2$, 2%/ PNP 2, 2% | RT, 12 h | 99% |
| 12 | piperidine | CH$_3$CH=CHCO$_2$Et | Pd(OAc)$_2$, 10% | RT, 12 h | 5% |
| 13 | | | Pd(TFA)$_2$, 10% | RT, 12 h | 71% |
| 14 | | | Pd(OAc)$_2$, 5%/ PCP 1, 5% | RT, 12 h | 54% |
| 15 | | | Pd(OAc)$_2$, 5%/ BINAP 5% | RT, 12 h | 68% |
| 16 | | | Pd(TFA)$_2$, 5%/ PNP 2, 5%/ | RT, 12 h | 76% |
| 17 | piperidine | CH$_2$=C(CH$_3$)CO$_2$Et | Pd(TFA)$_2$, 2% | RT, 18 h | 19% |
| 18 | | | Pd(TFA)$_2$, 2%/ PNP 2, 2% | RT, 12 h | 45% |
| 19 | | | Pd(TFA)$_2$, 2%/ BINAP, 2% | RT, 12 h | 80% |
| 20 | | | Pd(TFA)$_2$, 2%/ PPh$_3$, 4% | RT, 12 h | 82% |
| 21 | PhNH$_2$ | CH$_2$=C(CH$_3$)CN | Pd(OAc)$_2$, 10%/ PCP 1, 10% | 100° C., 48 h | 99% |
| 22 | | | Pd(OAc)$_2$, 2%/ PCP 1, 2% | 100° C., 72 h | 82% |
| 23 | | | Pd(TFA)$_2$, 10%/ PNP 2,10% | RT, 18 h | 88% |

TABLE 6-continued

| | | Transition metal-catalyzed addition of amines to activated olefins.[a] | | | |
|---|---|---|---|---|---|
| Entry | Amine | Olefin | Catalyst, mol% | Conditions | Yield[b] |
| 24 | PhNH$_2$ | CH$_2$=CH-CN | Pd(OAc)$_2$, 10%/ PCP 1,10% | 100° C., 36 h | 90% |

[a]Reactions were run on a 1 or 2 mmol scale.
[b]Yields are an average of two runs.

In Table 6, the PCP and PNP ligands have the following structures:

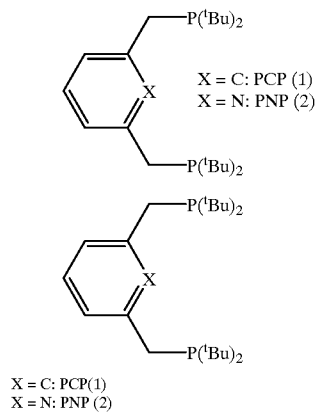

X = C: PCP(1)
X = N: PNP(2)

In all cases, control experiments without any catalyst that were run in toluene solvent at the temperatures and times required for the catalytic reactions proceeded to completion showed no reaction or less than 10% conversion. Yields for reaction of piperidine with methacrylonitrile using selected catalysts are provided as entries 1–7 in Table 6. Entries 1 and 2 demonstrate that the calorimetric assay is effective in distinguishing an active catalyst from a relatively inactive catalyst (see calorimetric assay below). Entries 3–7 confirm the activity of palladium complexes ligated by PCP and PNP ligands for this process, as well as the rhodium, iridium and ruthenium complexes in the absence of phosphine.

Entries 8 and 9 confirm the ability of the calorimetric assay to evaluate catalysts for the formation of secondary amine products (see calorimetric assay procedure below). As shown in entry 9, Pd(OAc)$_2$ and the PCP ligand 1 provide good yields of the addition product, and this reaction required the phosphine ligand. Reactions of piperidine with crotononitrile, ethyl crotonate, and ethyl methacrylate were also catalyzed by a combination of either Pd(OAc)$_2$ or Pd(TFA)$_2$ and phosphine ligand, but not by the rhodium, iridium or ruthenium complexes described above. The results of experiments with these substrates on a 1 mmol scale are summarized in entries 10–20. The combination of Pd(TFA)$_2$ and PNP 2 was the most effective of the complexes tested as a catalyst for the addition of piperidine to crotononitrile, while Pd(TFA)2 and either PNP 2 or BINAP most effectively catalyzed the addition of piperidine to ethyl crotonate. A combination of Pd(TFA)$_2$ and either BINAP or PPh$_3$ catalyzed the addition of piperidine to ethyl methacrylate at room temperature.

Colorimetric Assays:

1. High Throughput Analysis of the Addition of Aniline to 1,3-Cyclohexadiene: Stock solutions of metal complexes (30 µL, 0.0040 mmol of metal), ligands (30 µL, 0.0040 mmol for bisphosphines and 0.0080 mmol for monophosphines), aniline (9.1 µL, 0.10 mmol), 1,3-cyclohexadiene (19.0 µL, 0.20 mmol) and TFA (10 µL, 0.010 mmol) were loaded into a glass 96-well plate using a multichannel pipet. The 96-well plate was covered with a Teflon sheet and placed between two aluminum blocks. The blocks were then attached with bolts. The plate was then shaken using a rotary shaker for 4 h at room temperature. Aliquots that were 10 µL in volume were transferred to a new 96-well glass plate and to these aliquots was added 2-Furaldehyde (10.0 µL, 0.122 mmol) and acetic acid (50.0 µL, 0.870 mmol). The resulting red or yellow solutions were then diluted by adding THF and acetic acid to distinguish the colors and produce the solutions show in in FIG. 1.

Figure 2:
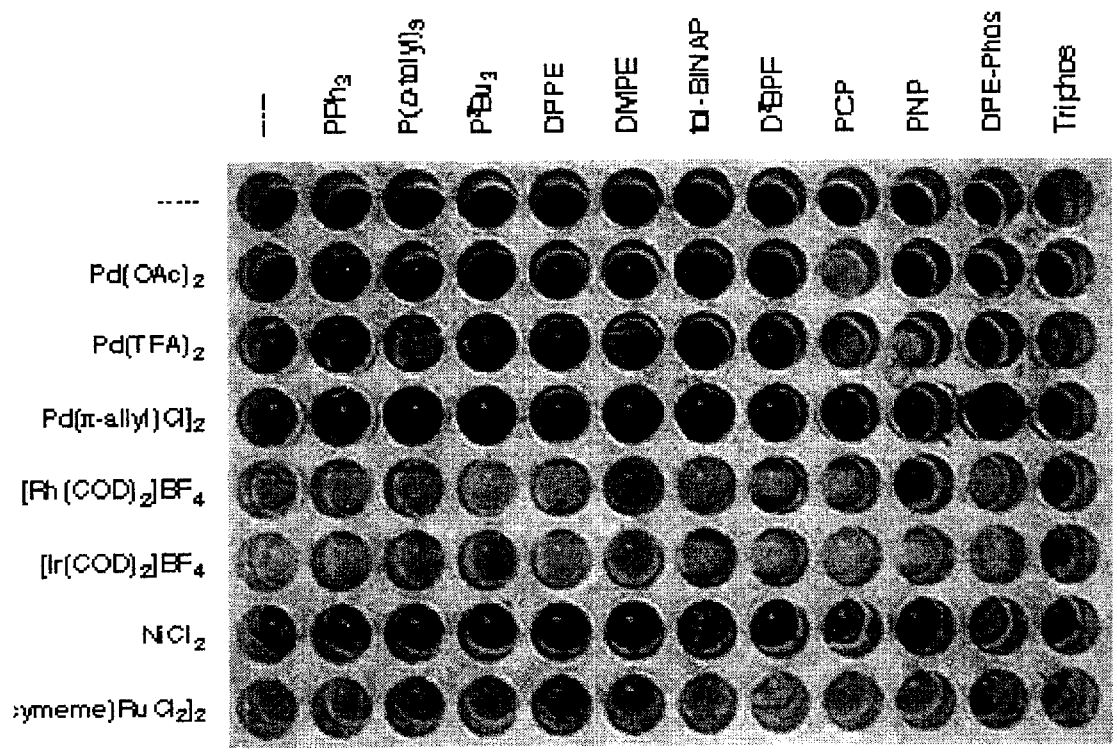
FIG. 2 shows the results of high-throughput analysis of transition metal catalysts that are potentially useful in the addition of piperidine to methacrylonitrile.

2. High-Throughput Analysis of the Addition of Piperidine to Methacrylonitrile: Stock solutions of metal complexes (16.0 or 32.0 µL, 0.0040 mmol), ligands (16.0 or 32.0 µL, 0.0040 mmol), piperidine (20.0 µL, 0.20 mmol) and methacrylonitrile (67.0 µL, 0.80 mmol) were loaded into a 96-well glass plate using a multichannel pipette. The 96-well plate was covered with a Teflon sheet and a glass slide, which was clamped to the plate. The plate was then shaken using a rotary shaker for 24 h at room temperature. Aliquots of the reaction mixture (15 µL) were transferred to another 96-well glass plate using a multichannel pipette. Acetaldehyde (15 µL, 0.270 mmol) and 20% Na$_2$Fe(CN)$_5$NO.2H$_2$O in saturated aqueous NaHCO$_3$ (30 µL) were then added to provide the calorimetric signal for the presence or absence of piperidine. The results are shown in FIG. 2.

In another Example, the reaction of octylamine with methacrylonitrile was evaluated after 12 h at room temperature using the same calorimetric assay. In this case, the blue color signified formation of a secondary alkyl amine product instead of consumption of starting material. Catalyst activity was easily assessed visually in a qualitative fashion using this method. However, the color faded after a few seconds in these reaction solutions, and a clear photograph of all reactions evaluated simultaneously was not recorded. The reaction between these substrates did not occur at room temperature using the iridium, rhodium, or ruthenium complexes described above, but did occur under these conditions in the presence of catalytic amounts of Pd(OAc)2 and PCP 1.

While the invention has been described in combination with embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims. All patent applications, patents, and other publications cited herein are incorporated by reference in their entireties.

What is claimed is:

1. A process for addition of amines to carbon-carbon double bonds in a substrate, comprising:

reacting an amine compound comprising a primary or a secondary amine with a compound containing at least one carbon-carbon double bond in the presence a transition metal catalyst and in the absence of an alkylaluminum co-catalyst under reaction conditions effective to form a product having a covalent bond between said primary or secondary amine and a carbon atom of the former said carbon-carbon double bond;

wherein the reaction time is less than 40 hours, and wherein said reaction produces more than 20 moles of product per mole of said transition metal in said catalyst, and consumes more than 30% of either of said amine compound or said compound containing at least one carbon-carbon double bond, and wherein said product contains at least 80% of one regioisomer, said transition metal catalyst comprising a Group 8 metal and a ligand containing one or more 2-electron donor atoms.

2. The process of claim 1, wherein said amine compound comprising a primary or a secondary amine is selected from the group consisting of aryl amines, cyclic amines, alkylamines, and combinations thereof.

3. The process of claim 2, wherein said aryl amines are selected from the group consisting of substituted or unsubstituted aniline, substituted or unsubstituted aminonaphthalene, substituted or unsubstituted anisidine, substituted or unsubstituted toluidine, and combinations thereof.

4. The process of claim 2, wherein said cyclic amines are selected from the group consisting of piperidine, morpholine, pyrrolidine, aziridine, azetidine, hexamethylene imine, and combinations thereof.

5. The process of claim 1, wherein said compound containing at least one carbon-carbon double bond is selected from the group consisting of vinylarenes, 1,3-dienes, acrylates, acrylonitriles, and combinations thereof.

6. The process of claim 5, wherein said vinylarenes are selected from the group consisting of substituted or unsubstituted styrenes, substituted or unsubstituted vinylnaphthalenes, and combinations thereof.

7. The process of claim 5, wherein said 1,3-dienes are selected from the group consisting of 2,3-dimethylbutadiene, isoprene, 1,3-cyclohexadiene, 1,3-cycloheptadiene, 1,3-cyclooctadiene, and combinations thereof.

8. The process of claim 5, wherein said acrylates are selected from the group consisting of ethylmethacrylate, methylcrotonate, acrylic acid esters, methylacrylonitrile, crotonitrile, and combinations thereof.

9. The process of claim 1, wherein said Group 8 metal is selected from the group consisting of palladium, platinum, and nickel.

10. The process of claim 1, wherein said ligand containing one or more 2-electron donor atoms is selected from the group consisting of unsaturated Group 15 heterocycles, Group 15-substituted metallocenes, Group 15-substituted alkanes, Group 15-substituted arylenes, and combinations thereof.

11. The process of claim 10, wherein said Group 15-substituted metallocene is a Group 15-substituted metallocene of iron, titanium, vanadium, chromium, manganese, cobalt, nickel, molybdenum, or ruthenium.

12. The process of claim 10, wherein said Group 15-substituted metallocene is a Group 15-substituted ferrocene.

13. The process of claim 12, wherein said Group 15-substituted ferrocene is 1,1'-bis(diphenylphosphino) ferrocene (DPPF).

14. The process of claim 10, wherein said Group 15-substituted arylene is a Group 15-substituted $C_{4-20}$ arylene.

15. The process of claim 14, wherein the Group 15-substituted arylene is 1,1'-bis(diphenylphosphino)-2,2'-binaphthyl (BINAP) or 1,1'-bis(di-p-tolylphosphino)-2,2'-binaphthyl (Tol-BINAP).

16. The process of claim 10, wherein said transition metal catalyst is selected from those having the formula $$(L)^1_{1-6}(L)^2_{1-6}MX_y$$

wherein $(L)^1$ and $(L)^2$ are ligands containing two-electron donor atoms, M is the Group 8 transition metal, each X is independently a monovalent anionic ligand or a divalent anionic ligand; and wherein y varies from 0 to 4.

17. The process of claim 16, wherein the transition metal catalyst is selected from the group consisting of [1,1'-bis(diphenylphosphino)binaphthyl]palladium (II) bis-triflate, [1,1'-bis(diphenylphosphino)binaphthyl]palladium (II) bis-trifluoroacetate, [1,1'-bis(diphenylphosphino)binaphthyl] palladium (II) bis-tosylate, and bis[1,1'-bis(diphenylphosphino)binaphthyl]palladium(0).

18. The process of claim 1, wherein said catalyst is prepared in situ in the reaction mixture.

19. The process of claim 18, wherein the catalyst is prepared from an allyl, carboxylate or alkene complex of a Group 8 transition metal complex or a Group 8 transition metal carboxylate combined with 1,1'-bis(diphenylphosphino)ferrocene, 1,1'-bis(di-c-tolylphosphino)ferrocene, or 1,1'-bis(diphenylphosphino)-2,2-binaphthyl.

20. The process of claim 19, wherein said allyl, carboxylate or alkene complex of the Group 8 transition metal is bis-(di(benzylidene)acetone) palladium, allyl palladium chloride dimer, palladium bis-trifluoroacetate, or bis-cyclooctadiene nickel.

21. The process of claim 1, wherein the catalyst is anchored or supported on a catalyst support.

22. The process of claim 1, wherein said reaction conditions further comprise a solvent selected from the group consisting of aromatic hydrocarbons, chlorinated aromatic hydrocarbons, ethers, water, and aliphatic alcohols.

23. The method of claim 1, wherein said reacting step takes place in the presence of acid.

24. The method of claim 1, wherein said transition metal catalyst is chiral and nonracemic, and wherein said product is nonracemic.

25. A process for enantioselective addition of amines to carbon-carbon double bonds in a substrate, comprising:

reacting an amine compound comprising a primary or a secondary amine with a compound containing at least one carbon-carbon double bond in the presence a chiral and nonracemic transition metal catalyst under reaction conditions effective to form a product having a covalent bond between said primary or secondary amine and a carbon atom of the former said carbon-carbon double bond; said transition metal catalyst comprising a Group 8 metal and a ligand containing one or more 2-electron donor atoms; and wherein said product is formed in greater than 20% yield, and with greater than 50% enantioselectivity.

26. The process of claim 25, wherein said amine compound comprising a primary or a secondary amine is selected from the group consisting of aryl amines, cyclic amines, alkylamines, and combinations thereof.

27. The process of claim 25, wherein said compound containing at least one carbon-carbon double bond is selected from the group consisting of vinylarenes, cyclic 1,3-dienes, acyclic 1,3-dienes, acrylates, acrylonitriles, and combinations thereof.

28. The process of claim 25, wherein said Group 8 metal is selected from the group consisting of palladium, platinum, and nickel.

29. The process of claim 25, wherein said ligand containing one or more 2-electron donor atoms is selected from the group consisting of unsaturated Group 15 heterocycles, Group 15-substituted metallocenes, Group 15-substituted alkanes, Group 15-substituted arylenes, and combinations thereof.

30. The process of claim 29, wherein said Group 15-substituted metallocene is a Group 15-substituted ferrocene.

31. The process of claim 29, wherein said Group 15-substituted arylene is 1,1'-bis(diphenylphosphino)-2,2'-binaphthyl (BINAP) or 1,1'-bis(di-p-tolylphosphino)-2,2'-binaphthyl (Tol-BINAP).

32. The process of claim 25, wherein said transition metal catalyst is selected from those having the formula $(L)^1{}_{1-6}(L)^2{}_{1-6}MX_y$ wherein $(L)^1$ and $(L)^2$ are ligands containing two-electron donor atoms, M is the Group 8 transition metal, each X is independently a monovalent anionic ligand or a divalent anionic ligand; and wherein y varies from 0 to 4.

33. The process of claim 32, wherein the transition metal catalyst is selected from the group consisting of [1,1'-bis (diphenylphosphino)binaphthyl]palladium (II) bis-triflate, [1,1'-bis (diphenylphosphino)binaphthyl]palladium (II) bis-trifluoroacetate, [1,1'-bis (diphenylphosphino)binaphthyl] palladium (II) bis-tosylate, and bis 1,1'-bis (diphenylphosphino)binaphthyl]palladium(0).

34. The process of claim 25, wherein said catalyst is prepared in situ in the reaction mixture.

35. The process of claim 34, wherein the catalyst is prepared from an alkene, diene, allyl, or carboxylate complex of a Group 8 transition metal complex or a Group 8 transition metal carboxylate combined with 1,1'-bis (diphenylphosphino)-2,2-binaphthyl or Ligand 1:

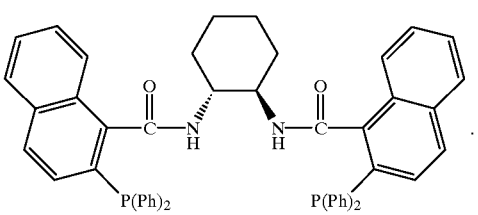

Ligand 1

36. The process of claim 35, wherein said alkene, allyl, or carboxylate complex of the Group 8 transition metal is selected from the group consisting of (allyl)palladium chloride dimer, palladium bis(di(benzylidene)acetone), dipalladium tris(di(benzylidene)acetone), palladium bis-trifluoroacetate, bis(cyclooctadiene)nickel, and combinations thereof.

37. The method of claim 25, wherein said reacting step takes place in the presence of acid.

38. A method for determining the activity of a catalyst useful in a reaction that adds primary or secondary amine compounds to compounds containing at least one carbon-carbon double bond, comprising:
  (1) reacting in a reaction vessel an amine compound comprising a primary or a secondary amine with a compound containing at least one carbon-carbon double bond in the presence a transition metal catalyst under reaction conditions effective to form a product containing a covalent bond between said primary or secondary amine and a carbon atom of the former said carbon-carbon double bond, said transition metal catalyst comprising a Group 8 metal and a ligand containing one or more 2-electron donor atoms;
  (2) adding a calorimetric agent to said reaction vessel, said calorimetric agent reactive with said amine compound or said product; and
  (3) evaluating the degree of color in said reaction vessel to determine the activity of said catalyst.

39. The method of claim 38, wherein said evaluation step measures the consumption of said amine compound.

40. The method of claim 39, wherein said calorimetric reagent comprises 2-furaldehyde and acetic acid, and wherein a low degree of color indicates an active catalyst.

41. The method of claim 38, wherein said calorimetric reagent comprises sodium nitroferricyanide(III) dihydrate and acetaldehyde, and wherein a low degree of color indicates an active catalyst.

42. The method of claim 38, wherein said evaluation step measures the production of said product.

43. The method of claim 42, wherein said calorimetric reagent comprises sodium nitroferricyanide(III) dihydrate and acetaldehyde, and wherein a high degree of color indicates an active catalyst.

44. The method of claim 38, wherein said adding step takes place during or after said reaction.

* * * * *